United States Patent [19]
Lin et al.

[11] Patent Number: 6,083,458
[45] Date of Patent: Jul. 4, 2000

[54] APPARATUS AND METHOD FOR PROVIDING FLUID TO DEVICES WITH REDUCED OR WITHOUT OCCLUSION

[75] Inventors: Szu-Min Lin, Laguna Hills; Paul Taylor Jacobs, Trabuco Canyon; Su-Syin S. Wu, Irvine; Nancy S. Chu, Laguna Niguel, all of Calif.

[73] Assignee: Ethicon, Inc., New Brunswick, N.J.

[21] Appl. No.: 08/992,603

[22] Filed: Dec. 17, 1997

[51] Int. Cl.$^7$ .................................................. A61L 2/18
[52] U.S. Cl. ........................... 422/33; 422/28; 422/292; 422/297; 422/300; 422/105
[58] Field of Search ................... 422/20, 28, 31, 422/33, 105, 292, 297, 298, 300, 305

[56] References Cited

U.S. PATENT DOCUMENTS

| | | |
|---|---|---|
| 3,814,901 | 6/1974 | Morhack . |
| 4,203,943 | 5/1980 | Gillis et al. . |
| 4,321,232 | 3/1982 | Bithell . |
| 4,337,223 | 6/1982 | Kaye . |
| 4,380,530 | 4/1983 | Kaye . |
| 4,410,492 | 10/1983 | Kaye . |
| 4,576,792 | 3/1986 | Martensson . |
| 4,579,597 | 4/1986 | Sasa et al. . |
| 4,731,222 | 3/1988 | Kralovic et al. . |
| 4,744,951 | 5/1988 | Cummings et al. . |
| 4,756,882 | 7/1988 | Jacobs et al. . |
| 4,892,706 | 1/1990 | Kralovic et al. . |
| 4,937,046 | 6/1990 | Andersen et al. . |
| 4,943,414 | 7/1990 | Jacobs et al. . |
| 4,956,145 | 9/1990 | Cummings et al. . |
| 5,017,241 | 5/1991 | Ryan . |
| 5,037,623 | 8/1991 | Schneider et al. . |
| 5,077,008 | 12/1991 | Kralovic et al. . |
| 5,091,343 | 2/1992 | Schneider et al. . |
| 5,114,596 | 5/1992 | Laterra . |
| 5,116,575 | 5/1992 | Badertscher et al. . |
| 5,186,893 | 2/1993 | Moulton et al. . |
| 5,209,909 | 5/1993 | Siegel et al. . |
| 5,217,698 | 6/1993 | Siegel et al. . |
| 5,225,160 | 7/1993 | Sanford et al. . |
| 5,260,021 | 11/1993 | Zeleznick . |
| 5,266,275 | 11/1993 | Faddis . |
| 5,279,799 | 1/1994 | Moser . |
| 5,310,524 | 5/1994 | Campbell et al. . |
| 5,348,711 | 9/1994 | Johnson et al. . |
| 5,350,563 | 9/1994 | Kralovic et al. . |
| 5,374,394 | 12/1994 | Kralovic . |
| 5,391,360 | 2/1995 | Kochte et al. . |
| 5,407,648 | 4/1995 | Allen et al. . |
| 5,407,685 | 4/1995 | Malchesky et al. . |
| 5,441,707 | 8/1995 | Lewis et al. . |
| 5,443,801 | 8/1995 | Langford . |
| 5,445,792 | 8/1995 | Rickloff et al. . |
| 5,492,671 | 2/1996 | Krafft . |
| 5,494,530 | 2/1996 | Graf . |
| 5,505,218 | 4/1996 | Steinhauser et al. . |
| 5,508,009 | 4/1996 | Rickloff et al. . |
| 5,527,508 | 6/1996 | Childers et al. . |
| 5,534,221 | 7/1996 | Hillebrenner et al. . |
| 5,540,901 | 7/1996 | Riley . |
| 5,552,115 | 9/1996 | Malchesky . |
| 5,556,607 | 9/1996 | Childers et al. . |
| 5,580,530 | 12/1996 | Kowatsch et al. . |
| 5,609,821 | 3/1997 | Grimberg et al. . |
| 5,753,195 | 5/1998 | Langford et al. ..................... 422/292 |

FOREIGN PATENT DOCUMENTS

3416743 A1  7/1985  Germany .

*Primary Examiner*—Robert J. Warden, Sr.
*Assistant Examiner*—Fariborz Moazzam
*Attorney, Agent, or Firm*—Knobbe, Martens, Olson & Bear, LLP

[57] ABSTRACT

A system for providing fluid to a device comprises an interface separating a first space from a second space. The interface has at least one opening for receiving the device. The opening has a contact surface which contacts the device forming a contact area. Means for enhancing penetration of the fluid to the contact area is coupled to the opening. This system significantly reduces or total eliminates the occlusion area on the surface of the device.

32 Claims, 19 Drawing Sheets

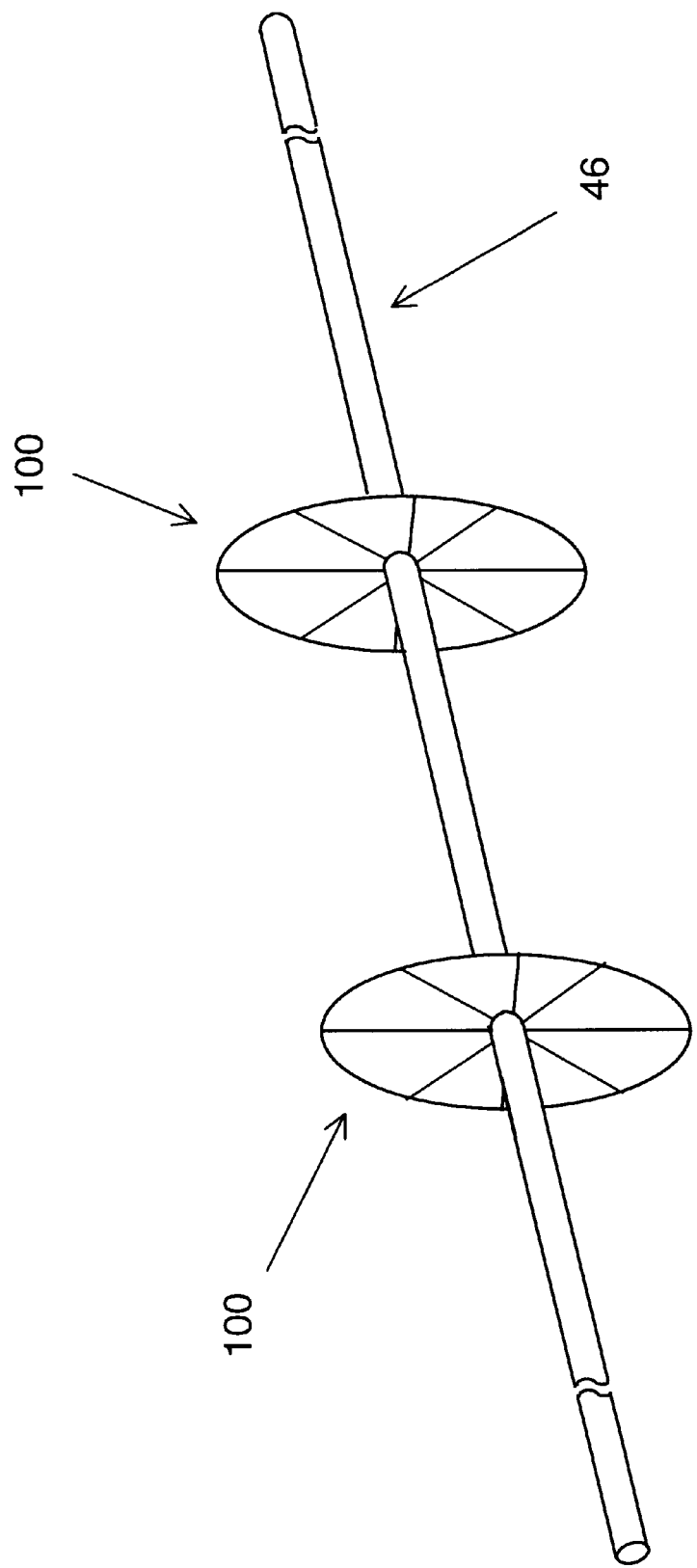

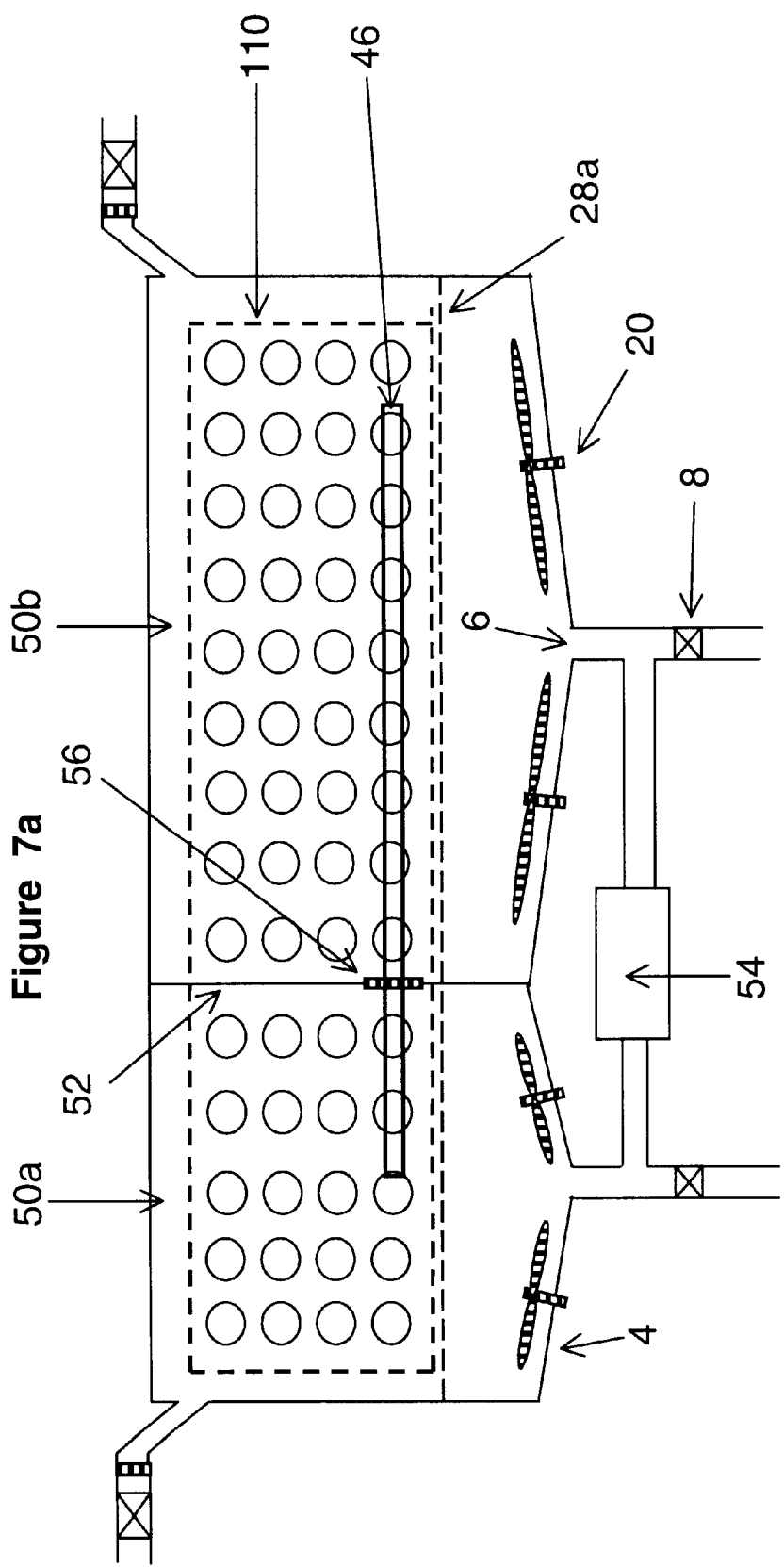

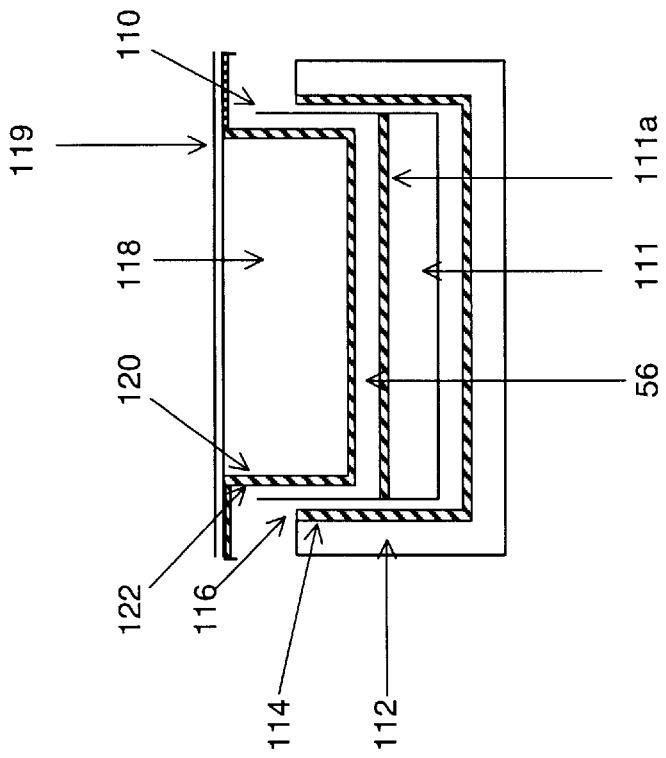
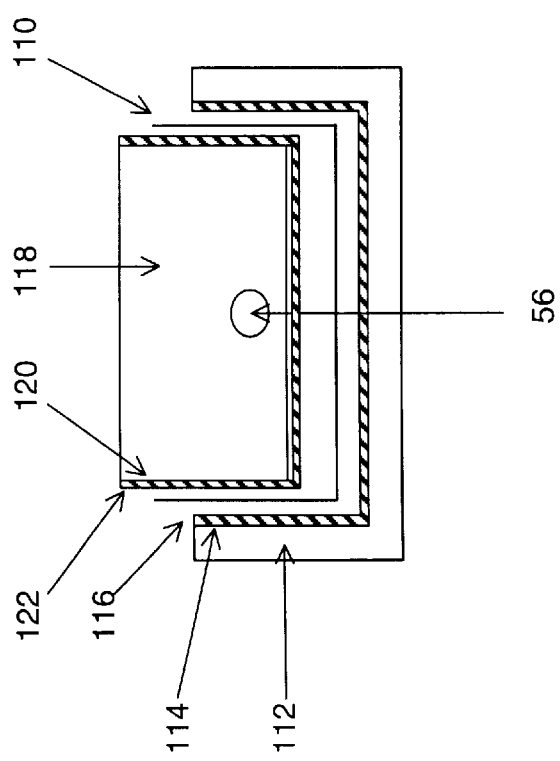

APPARATUS AND METHOD FOR PROVIDING FLUID TO DEVICES WITH REDUCED OR WITHOUT OCCLUSION

FIELD OF THE INVENTION

The invention relates to providing fluids, such as sterilization fluids, to articles including medical instruments having long narrow lumens, and, more particularly, to an apparatus and method for delivering an antimicrobial fluid more effectively to contact surfaces which are otherwise occluded from the sterilization fluid during a sterilization process.

BACKGROUND OF THE INVENTION

Chemical sterilization uses a sterilizing fluid such as hydrogen peroxide, ethylene oxide, chlorine dioxide, peracetic acid, or a combination thereof. A plasma may be induced to enhance the sterilization process. Although chemical sterilization is normally effective, it is difficult for cleaning and sterilizing fluid to penetrate to the contact area of the device to be sterilized. It also may not be as effective with medical devices containing long, narrow tubes, or lumens. Sterilization of these long lumens requires that the sterilizing agent penetrate the entire length of the long narrow tube. It is difficult for the sterilizing agent to completely penetrate these long narrow tubes. In order to enhance the penetration of the sterilizing agent down the entire length of the lumen, several forms of apparatus have been developed to flow sterilizing agent through the length of the lumen, thus enhancing the effectiveness of the sterilizing treatment.

For example, U.S. Pat. Nos. 4,410,492 and 4,337,223 describe a sterilization method in which the lumen is placed in a socket connected to a valve and a recirculating pump. The sterilizing gas is recirculated from the sterilization chamber through the lumen of the instrument. Although the method is effective at sterilizing the lumen, sterilization of endoscopes requires 2–3 hours using ethylene oxide as the sterilizing gas.

A method which delivers sterilizing agent down long, narrow lumens is described in U.S. Pat. No. 5,580,530. The lumen is inserted into an adaptor connected to a vessel containing hydrogen peroxide called the booster. The lumen, adaptor, and booster are all placed in the sterilization chamber. When the sterilization chamber is evacuated during the sterilization procedure, the hydrogen peroxide in the booster vaporizes and passes through the lumen, thereby sterilizing the interior of the lumen.

During use of the various sterilization methods, there are always areas of contact between the device to be sterilized and a holding or supporting means. It is difficult for a fluid such as a cleaning solution or a sterilizing agent to penetrate into these contact areas. Thus, the contact area usually can not be sterilized efficiently in a conventional sterilization process.

There is a need for a method of enhancing the penetration of washing, rinsing and/or sterilizing fluids into these contact areas, or significantly reducing or totally eliminating the occluded area to allay any potential concerns about incomplete sterilization.

SUMMARY OF THE INVENTION

In one aspect, the present invention relates to a system for providing fluid to a device. This system includes an interface separating a first space from a second space. The interface has at least one opening for receiving the device. The opening has a contact surface which contacts the device at a contact area. A means for enhancing penetration of fluid to the contact area is coupled to the opening. This means can be any of the various such means for accomplishing this result which are disclosed herein, or any equivalents thereof.

Another aspect of the present invention is a method for providing fluid to a device. The method involves providing a surface having a means for enhancing penetration of fluid between the surface and the device at a contact area on the surface. As in the previous aspect of the invention, this means can be any of the various such means for accomplishing this result which are disclosed herein, or any equivalents thereof. The device is placed in or on the surface such that the device contacts the surface at the contact area. Fluid is then provided to the device such that the fluid penetrates the contact area and contacts the device.

A further aspect of the invention relates to another method for providing fluid to a device. This method involves the steps of:

(a) providing an interface;

(b) providing an opening within the interface;

(c) placing the device in the opening such that the device contacts the interface at a contact area on the interface;

(d) providing the fluid to the device; and (e) changing the relative position of the device with respect to the opening such that the device does not contact the contact area.

BRIEF DESCRIPTION OF THE DRAWINGS

FIG. 3b is a schematic diagram of a shutter used in the interface of the container of FIG. 3a.

FIG. 3c is a schematic diagram of a iris valve used in the interface of the container of FIG. 3a.

FIGS. 3d, 3e, and 3f are schematic diagrams of two plates forming an opening in the interface of the container of FIG. 3a.

FIG. 3g is schematic diagram of an interface of the container of FIG. 3a.

FIGS. 5b and 5c are schematic diagrams of two holders of the container shown in FIG. 5a holding a lumen device.

FIG. 7a is a schematic diagram of a container having an interface and a tray across the interface according to the present invention.

FIGS. 7b and 7c are cross-sectional views of the container of FIG. 7a at the location of the interface.

FIG. 8a is a top view of the container of FIG. 7a.

FIG. 8b is a top view of a portion of the interface of FIG. 7a.

FIG. 8c is a top view of the tray of FIG. 7a.

DETAILED DESCRIPTION OF THE PREFERRED EMBODIMENT

Figure 1A:
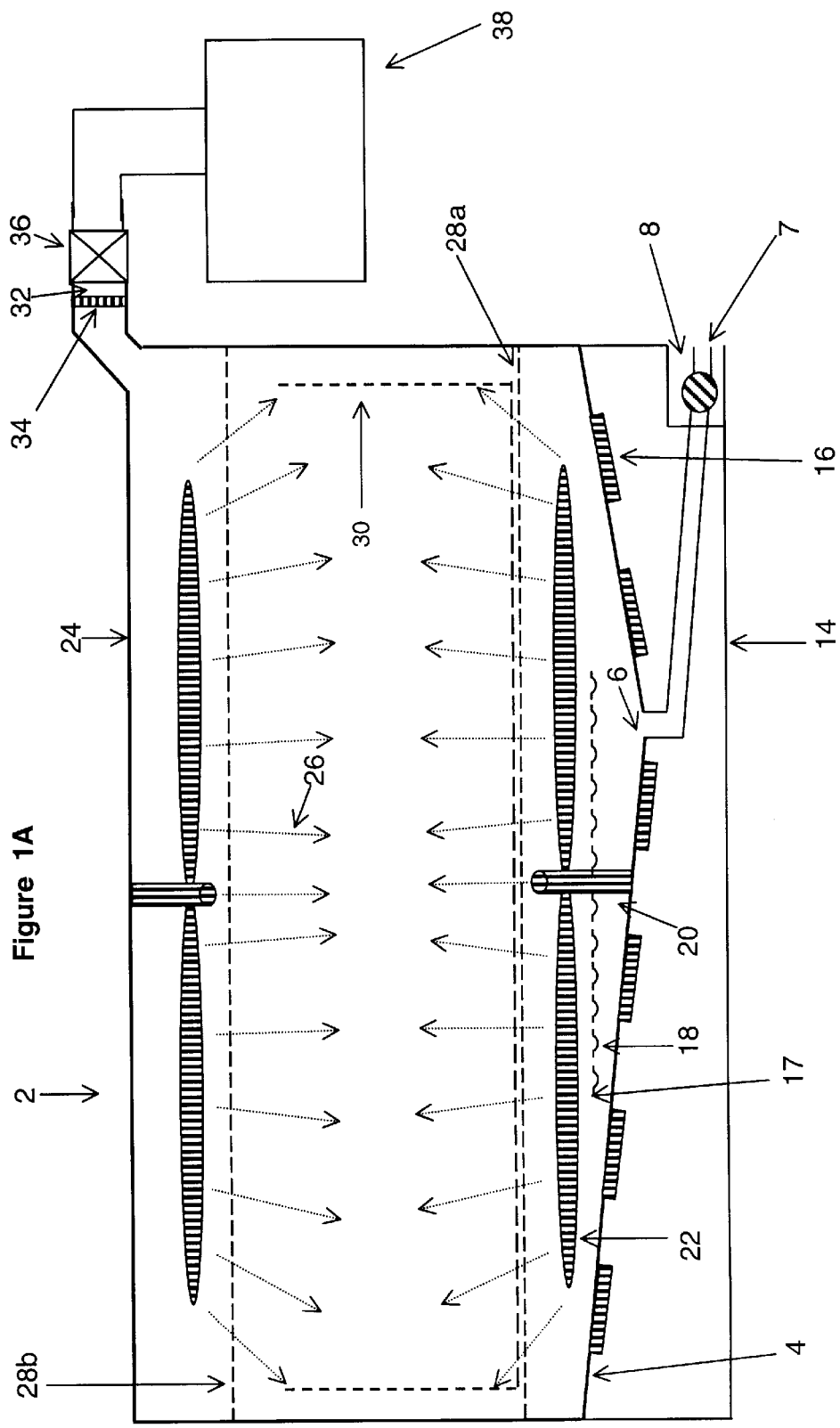
FIG. 1a is a schematic diagram of a container used in a cleaning/sterilizing process of the present invention.

The method and apparatus of the present invention can be used to eliminate occlusion area of a device to be rinsed, cleaned and/or sterilized/disinfected, which area is occluded from exposing to the fluid used for this purpose, or to reduce the contact area between the device and a mechanism for holding the device. As will be appreciated by those having ordinary skill in the art, such a fluid can be a vapor or gas, including plasma, or a liquid. The device can be a lumen device, including a device hving multiple lumens, or a non-lumen device. However, more often the procedures of the present invention are used for lumen devices, specially devices with long narrow lumens.

As will be described later in more details, in the cleaning/sterilization of a lumen device, a preferred process is to generate a flow of sterilant through the lumen. Two open ends of the lumen device usually are located in two compartments or spaces separated by an interface. The lumen device is placed passing through an opening on the interface. In the case of a non-lumen device, the device to be cleaned or sterilized is usually placed on a grid or a tray. The tray, grid, or any other means for supporting the device are also referred as an interface. Thus, the terms "opening" and "interface" as used throughout the specification are to be construed broadly. For example, the interface can be one or more plates of various shape, an adaptor, a connector, a tray, a grid, a mat, a separator, or any other proper forms. A variety of interfaces used in the present invention will be discussed later in more details. As an example, a mat with elongated projections extending from its surface is used as an interface in the present invention. A device to be cleaned or sterilized is placed on the surface of the mat and supported by the projections so that contact area between the device and the mat is reduced. Openings are formed between the projections. Such mat is commercially available from Advanced Sterilization Products (Part No. 99201–99211). The surface of the projections can be textured to further reduce contact area and enhance the penetration of fluid to the device surface. The compartment or space can be a container, an enclosure, a chamber, a fluid source, or a vacuum source. The two spaces separated by the interface can be insulated or sealed from each other, also can be in fluid communication with each other. As strong agitation and pressure differential between two compartments are often involved for a lumen device, the lumen device needs to be held by the opening or a holder coupled to the opening in order to keep the lumen device in position as well as keep the pressure differential during a sterilization process or other related process such as cleaning and rinsing.

The contact area between the contact surface of the device and the contact surface of the interface or the opening or the holder is hard to reach by either liquid or vapor because of the close contact between the two surfaces. Thus, the cleaning and sterilizing of a contact area is adversely affected by such occlusion. As used herein, if a contact area of a device to be sterilized is occluded from sterilant throughout an entire sterilization process, it is referred as an occlusion area. Several approaches are employed in the present invention to deal with this occlusion problem.

One approach is to reduce the contact area by using textures, sharp projections, or sharp edges on the contact surface of the opening of the interface, or on the contact surface of an adaptor, or a connector, or a holder. In this way, cleaning and sterilizing fluid can either flow or diffuse to most part of the contact surface of the device which is held by the holding mechanism and, in the meantime, the contact area between the opening and the device surface will impose a resistance to fluid flow high enough to allow a pressure difference to exist between the two spaces or compartments separated by the interface. Thus, a flow through the lumen of the device can be generated and maintained if desired. Another advantage of this approach is that the contact area generated through the above means can be controlled to provide a diffusion restricted environment at the contact area, which will increase the efficiency of the sterilization process as will be described in more details later.

Another approach is to use multiple holders in one single opening of the interface. For example, two apertures or two holders can be secured to a single opening forming a portion of the opening. Preferably, each of the holders is independently controllable and sealable. During a cleaning or sterilizing process, the two holders are alternately opened and closed, i.e. one is open while the other is close. In this way, a good seal between the two compartments in two sides of the interface can be maintained and the device can be held tightly during a sterilization process. Meanwhile, the contact areas on the device surface caused by the two holders are exposed to cleaning or sterilizing fluid alternately.

Still another approach is the combination of the above two approaches. In this approach, the contact surface of an interface, or of an opening of the interface, has multiple contact points or segments. The contact points can be projections, teeth, blades, sharp edges, or any other suitable forms and shapes. These contact points can be moveable and controlled separately so that a portion of the contact points is made in contact with the device to be sterilized while the others are not. By alternately changing the position of the contact points, or changing the position of the device relative to the contact points, all the occlusion areas will be exposed to the fluid. An example of such a multiple contact point structure is a shutter with multiple blades. Those blades can be separately controlled for opening and closing.

Besides, the occlusion area caused by a holding mechanism, occlusion also occurs where the device touches the cleaning or sterilizing apparatus, such as the bottom surface of a container, a tray, or a grid. In order to eliminate this kind of occlusion, moveable supporting pieces can be provided on the location in the apparatus where the device is placed. These supporting pieces are preferably separately controllable so that they can be alternately moved to and away from the device.

The elimination or reduction of the occlusion area is intended to improve the sterilization of the occluded exterior area of a device. Clearly, a good sterilization procedure is required to achieve an efficient sterilization. The present invention also provides a variety of apparatus and method for cleaning/sterilization of medical instruments with or without lumens.

The sterilization process without occlusion or with reduced occlusion of the present invention can be carried out with various apparatus and incorporated with various sterilization methods, which are described below.

Method to Deliver a Predetermined Amount of Liquid Sterilant

This method can be incorporated into the cleaning/sterilizing or cleaning/disinfecting process of the present invention. In order to maximize the efficiency of a vapor sterilization process, it is important and desirable to drain excess sterilant solution and only keep a desired amount of the sterilant solution to vaporize after treating a device to be sterilized with the sterilant solution.

According to the present invention, a sterilization container or enclosure may have a surface with wells thereon which define a known volume. The well is positioned so that when a liquid sterilant is introduced onto the surface, a known volume of the liquid sterilant fills the well and when the liquid sterilant is drained from the surface, the known volume of liquid sterilant remains in the well so that a subsequent vapor sterilization process can be performed on the device with the known volume of liquid sterilant positioned within the surface. The surface preferably has at least one perforation for draining the liquid sterilant from the surface. The well formed in the surface can be curved, flat or angled. Thus, the well can be an inwardly extending hemispherical projection. The well can also be formed in the surface as an inwardly extending rectangular projection having rounded ends. The well formed in the surface can also be a rectangular box having side walls, defining an opening. Where perforations are provided, they can be disposed adjacent the well, and can be roughly spherical in shape. The upwardly extending projection can include a perforation thereon, which can be on top of the projection or on a side of the projection. The surface can be a sloped surface, a convex or concave surface or a V-shaped surface. The surface can be made of a variety of materials including stainless steels, aluminum, aluminum alloys, liquid crystal polymers, polyesters, polyolefins polymers or fluorinated polyolefins. If the surface is comprised of a composite material, the composite material can include a filler of high thermal conductivity. Examples of composite materials include a metal-filled polymer, a ceramic-filled polymer and a glass-filled polymer. Those materials are also suitable for the side walls and doors of the sterilization container.

A tray with wells with configurations similar to that described above can be provided with a container or enclosure. The tray can be secured to the container or removably placed in the container.

Method Based on Diffusion Restricted Environments

A method of vapor sterilization or disinfection under diffusion-restricted environments can also be used in corporation with the cleaning/sterilizing or cleaning/disinfecting process of the present invention. In this method, the devices (lumen or non-lumen) to be sterilized are pretreated with a sterilant solution, and then exposed to pressures less than the vapor pressure of sterilant. Both the exterior and interior surface areas of a lumen or non-lumen device can be effectively sterilized by taking advantage of the diffusion-restricted environments within lumens or within a container or enclosure.

As used herein, a "diffusion-restricted" area refers to any one or more of the following properties: (1) the ability of the area of an article placed within the sterilization system of the present invention to retain 0.17 mg/L or more hydrogen peroxide after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the starting 1 mg/L hydrogen peroxide solution initially placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

This method includes the steps of contacting the exterior and interior of a device with a sterilant solution, and then exposing the device to a negative pressure or vacuum for a period of time sufficient to effect complete sterilization. For example, when 1 mg/L of hydrogen peroxide is used as sterilant, if the exposing step is conducted for 1 hour at 40° C. and 10 torr, the diffusion restricted area preferably retains 0.17 mg/L or more hydrogen peroxide, or retains 17% or more of the hydrogen peroxide placed therein after the exposing step. In certain preferred embodiments, the diffusion-restricted area has the same or more diffusion restriction than provided by a lumen 27 cm in length and an internal diameter of 3 mm, or has the same or more diffusion restriction than provided by a lumen having a ratio of length to internal diameter greater than 50. The contacting step can be performed by either a direct or an indirect contact procedure. Direct contacting includes methods such as injection, static soak, flow-through, condensation of a vapor, or aerosol spray, or mist spray. Any other methods involving physically contacting the devices to be sterilized with a sterilant would be considered direct contacting. Indirect contacting includes those methods in which sterilant is introduced into the chamber or container, but not directly on or on the devices to be sterilized. The exposing step is preferably performed for 60 minutes or less, and is preferably performed at a pressure less than the vapor pressure of the sterilant. Thus, the preferred pressure range under conditions of the present invention is between 0 and 100 torr. The exposing step can include the step of heating the device, such as by heating the container in which the exposing step occurs. The container can be heated to about 40° C. to about 55° C. Alternatively, the sterilant solution can be heated, such as to a temperature of about 40° C. to about 55° C. Optionally, the step of exposing the device to a plasma can be conducted during the step of exposing the device to negative pressure or vacuum. In one embodiment employing exposure to plasma, the method is performed within a first chamber and the plasma is generated in a second separate chamber. This embodiment further comprises the step of flowing the plasma into the first chamber. Advantageously, the contacting and/or exposing steps of the method can be repeated one or more times.

Method Based on Controlled Pump-Down Rate

The cleaning/sterilizing process of the present invention can also be carried out in cooperation with a controlled pump down method without relying on a diffusion-restricted environment.

Effective sterilization results similar to those created in diffusion-restricted environments can be created through controlling the evacuation rate of a chamber or container in which devices to be sterilized are placed. Thus, in one embodiment of the present invention, this controlled pump-down rate method comprises the steps of contacting the device with a liquid sterilant at a first pressure; draining excess liquid sterilant to retain a predetermined amount of the sterilant, and decreasing the pressure of the chamber to a second pressure below the vapor pressure of the liquid sterilant in which at least a portion of the decrease in pressure below about the vapor pressure of the liquid sterilant occurs at a pump down rate of less than 0.8 liters per second, calculated based on the time required to evacuate the chamber from atmospheric pressure to 20 torr when the chamber is empty and dry, i.e. when the chamber has neither devices to be sterilized nor a visible quantity of liquid within it. According to one aspect of this preferred embodiment, at least the decrease in pressure below about two times the vapor pressure of the liquid sterilant occurs at a pump down rate of less than 0.8 liters per second. According to another embodiment, the decrease in pressure below about four times the vapor pressure of the liquid sterilant occurs at a pump down rate of less than 0.8 liters per second. Preferably, the pump down rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. The hydrogen peroxide usually is a solution as used in the art, preferably it is a 3–60% solution. The device can be a lumen or non-lumen medical instrument.

The present invention can also incorporate a method for sterilizing a device comprising the steps of (a) contacting the device with liquid sterilant at a first pressure; (b) retaining a predetermined amount of the liquid sterilant in the container; (c) pumping down the container or chamber to a second pressure which is lower than the first pressure at a first rate; and (d) pumping down the container or chamber to a third pressure which is lower than the second pressure, wherein at least a portion of the pumping down to the third pressure is at a second rate which is slower than the first rate. The pump down rate either above and/or below the second pressure can be constant or variable. In certain embodiments, the pump down rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pump down rate in step (d) is 0.8 liters/sec or less; more advantageously 0.6 liters/sec or less; even more advantageously 0.4 liters/sec or less; and most advantageously 0.2 liters/sec or less, calculated based on the time required to evacuate the chamber from atmospheric pressure to 20 torr under empty and dry conditions. Preferably, the liquid sterilant is hydrogen peroxide. In another embodiment, the device is a medical instrument having a lumen. Preferably, the pumping down of step (c) reduces the pressure to less than about three times, more preferably to less than about two times, the vapor pressure of the liquid sterilant.

Another suitable method includes contacting the device with liquid sterilant, retaining a predetermined amount of the liquid sterilant in the container, and reducing the pressure of the chamber while regulating the pump down rate so as to control the evaporation rate of sterilant in said chamber. In any of the methods described above, the contacting step may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting step in these methods can be either by direct or indirect contacting. As stated herein, indirect contacting involves introducing sterilant into the chamber without directly contacting the device to be sterilized.

Two Step Pump-Down Method

A two step pump down sterilization method can also be used in cooperation with the cleaning/sterilizing process of the present invention. This method comprises the steps of contacting a device with liquid sterilant; draining excess liquid sterilant to retain a predetermined amount of the sterilant; bringing the pressure of the chamber to a first pressure range at which the liquid sterilant is vaporized from non-diffusion restricted area of the device to sterilize the non-diffusion restricted area; bringing the pressure of the chamber to a second pressure range at which the liquid sterilant is vaporized from diffusion restricted area of the device to sterilize the diffusion restricted area, wherein the minimum pressure in the second pressure range is lower than the maximum pressure in the first pressure range.

Preferably, the first pressure range is from 20 to 760 torr; more preferably, the first pressure range is 20 to 80 torr; most preferably, the first pressure range is 40–50 torr. Advantageously, the second pressure range is 1–30 torr; more advantageously, the second pressure range is 5–10 torr. In one preferred embodiment, the device includes a diffusion-restricted environment. Preferably, the device is a medical instrument with a lumen. Advantageously, the sterilant is hydrogen peroxide. According to another aspect of this preferred embodiment, the chamber is at a set temperature and wherein the first pressure is preferably lower than the vapor pressure of the sterilant at the set temperature. Preferably, the pressure of the chamber is maintained constant at the first pressure for a time period sufficient to sterilize the non-diffusion restricted area. Advantageously, the pressure of the chamber is maintained constant at the second pressure for a time period sufficient to sterilize the diffusion restricted area. The pressure of the chamber may be permitted to increase after reaching the first or second pressure range as a result of vaporization of the sterilant within said chamber. Alternatively, the pressure of the chamber is permitted to decrease after reaching the first or second pressure through pumping of said chamber at a rate slower than used to decrease the pressure between said first and second pressure ranges. Preferably, the contacting step is with liquid, condensed vapor, or mist. The method can also include the steps of bringing the pressure to a third pressure lower than the second pressure to remove residual sterilant and/or exposing the device to plasma to remove residual sterilant or enhance sterilization efficacy.

Method Involving Direct Flow Through a Lumen of the Device to Be Sterilized

A method of directly flowing fluid through a lumen of a medical device to be treated can be incorporated with the cleaning/sterilizing or cleaning/disinfecting process of the present invention. An apparatus can be used to efficiently clean and sterilize devices with long narrow lumens by flowing a fluid such as a cleaning solution or a sterilant, either in liquid phase or in vapor phase, directly through the lumens of lumen devices to be sterilized.

The flow of a germicide (solution or vapor), or any cleaning solution through a lumen of a medical device is driven by a pressure drop between two open ends of the lumen. The pressure drop can be generated by applying either a vacuum or a high pressure at one end. By generating a forced flow through a pressure differential other than relying on diffusion, the sterilization rate is significantly increased and less time is needed for a sterilization cycle.

It is clear that the two ends of the lumen need to be exposed to a pressure differential. This is achieved in the present invention by placing a sealable interface between two chambers, two enclosures, or a container and an enclosure to separate them from each other. Preferably, an opening is provided in the interface and the lumen device to be sterilized is placed through the opening so that the lumen serves as a flow path between the two chambers or between the container and the enclosure.

The opening can be constructed in several ways. One way to achieve this is with a camera shutter approach employing an iris diaphragm, such as a precision iris diaphragm from Edmund Scientific. An optional spring can be used to secure the closure of the shutter. Also commercially available is Syntron Iris Flow Control Valve manufactured by FMC Corporation. This Iris Valve has a sleeve made of Teflon or other synthetic material defining an aperture. By rotating two ends of the sleeve relative to each other, the aperture can be reduced or increased. Iris diaphragm valves from Kemutec Inc. are also commercially available which can be automatically controlled. Another example is the AirGripper and AirPicker manufactured by Firesone Industrial Products Company. Another way to construct an openable and closeable opening is to employ two plates. Two edges of the two plates form a gap which can be adjusted by moving the two plates relative to each other. One or more lumen devices are placed through the gap formed between the two plates and the two plates are moved together to form a seal around the lumen devices. The edges of the two plates forming the gap can be equipped with compressible material or expandable material. When expandable material is used, a fluid source can be provided to expand the expandable material. Optionally, a porous material like a sponge or air permeable material may be utilized on the edges. In this case some sterilant can diffuse through the porous material to the outer surface of the lumen device occluded by the closed opening. However, most the sterilant flows through the lumen device. Another usable interface is a hole or a slot, the hole or slot is equipped with gas or liquid inflatable material so that by inflating the inflatable material on the hole or the slot the opening is reduced and the lumen device is held and sealed. Still another option is to place a compressible material on top of an expandable or inflatable material so as to facilitate the sealing around the lumen device.

The closing and opening movement of the opening can be controlled mechanically or electronically with any conventional mechanism. The degree of opening is adjustable. Thus, it can be sealed to a different degree between the opening and the lumen device depending on the desired purpose. For example, the opening can form a gas-tight seal, a tight-fitting seal, or a loose-fitting seal around the lumen device. As used herein, a gas-tight seal refers to a seal that substantially stops liquid and gas flow through the contact area between the opening and the lumen device surface. When a gas-tight seal is employed, preferably the device to be sterilized is first pre-cleaned so that the occluded area by the seal is cleaned before the gas-tight seal is formed. A loose-fitting seal allows both liquid and gas to flow through the gap between the opening and the lumen device surface, and in the meantime is able to maintain a pressure drop across the interface enough to generate a flow through the lumen. A tight-fitting seal allows gas and liquid to penetrate to the contact area between the opening and the lumen device surface by diffusion. For example, a tight-fitting seal can be formed with porous material or textures provided on the contact surface of the opening. Thus, for gas-tight seal the device is held tightly by the closed opening. In the tight-fitting seal, the closed opening also holds the device in position. In the case of a loose-fitting seal, the device can move relative to the opening, but is not flashed away.

The interface can be made openable, closeable, and removable, and may have more than one opening. In order to promote sterilization efficiency, all the sterilization apparatus of the present invention can be further equipped with a heater and/or a plasma.

Apparatus and methods of the present invention are described in more detail by reference to the drawings. In the following figures like numbers refer to like parts throughout. As used herein, the terms "container" and "enclosure" are exchangeable.

Figure 1C:
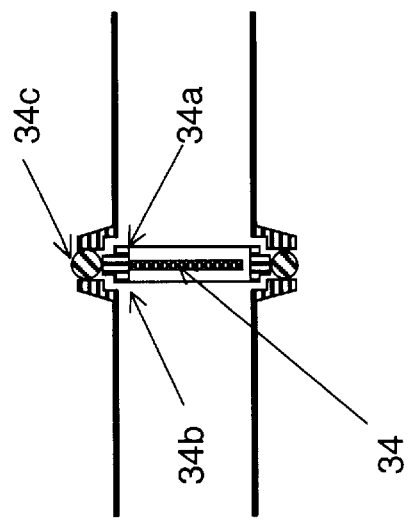
FIG. 1c is a schematic diagram of a gas-permeable but microorganism-impermeable barrier installed in a vacuum port of the container of FIG. 1.
Figure 1B:
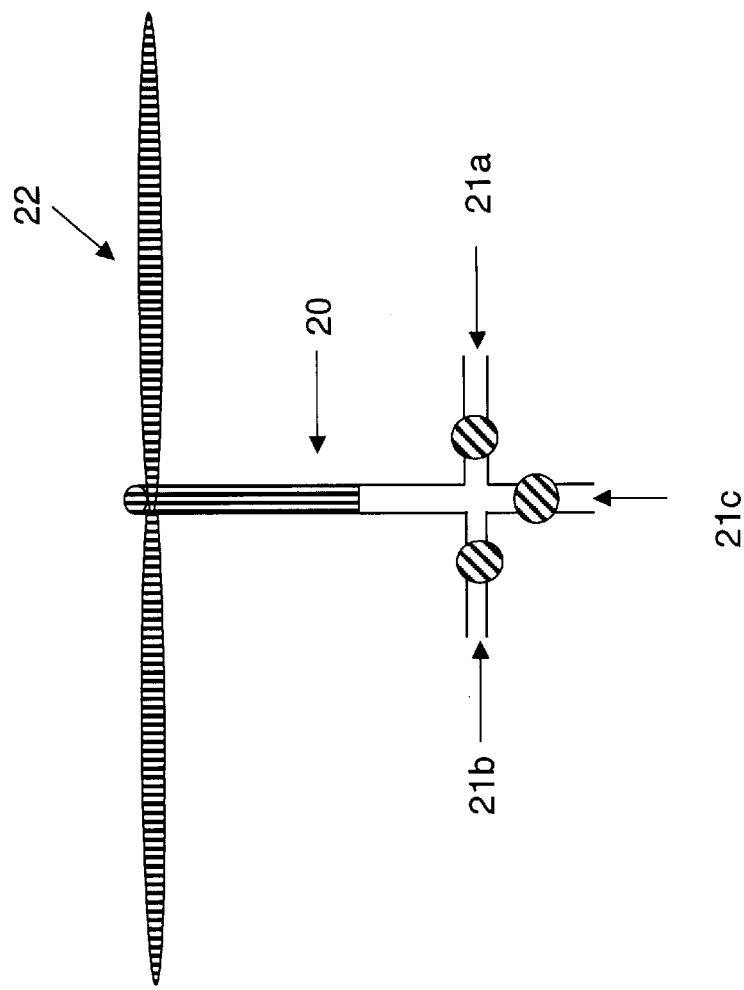
FIG. 1b is a schematic diagram of a stirrer with fluid inlets used in the container of FIG. 1.

FIG. 1a shows a container 2 used in a cleaning/sterilizing process of the present invention. Container 2 has a sloped bottom wall 4 leading to a fluid source 7. A fluid port 6 is provided at the lowest point of sloped bottom wall 4. Apparently, sloped bottom wall 4 can be configured differently and the lowest point can be located in any location within the sloped bottom wall 4. For example, instead located in the position as shown in FIG. 1a, the lowest point, thus the fluid port 6, can be located at one end or a corner of the sloped bottom wall 4. A valve 8 is provided at fluid port 6 to control fluid flow in and out container 2. Below sloped bottom wall 4 is a flat lower bottom 14. The lower surface of the sloped bottom wall 4 is equipped with a number of transducer 16 for providing ultrasonic cleaning. A number of wells 18 are provided on a plate 17 located above the upper surface of the sloped bottom wall 4 and below rotating arm 22. Plate 17 can be of any appropriate shape and made rotatable, so that unwanted liquid retained in wells 18 can be removed by rotating plate 17. Well 18 can have different shapes and is capable of retaining a predetermined amount of sterilant as described earlier. Plate 17 can be removably placed on the upper surface of the sloped bottom wall 4 or secured to the upper surface in a horizontal orientation. One or more stirrer 20 is installed either on sloped bottom wall 4 or on an upper wall 24 or on both. Rotating arm 22 of the stirrer 20 can be made hollow or contains channels connecting to an outside fluid source through the body of the stirrer 20. As shown in FIG. 1*b*, stirrer 20 can be connected to a water source 21*a*, an air source 21*b*, and a drain 21*c*, each of them is controlled by a valve. Water jet or air jet 26 can be provided through the channels of rotating arm 22. Container 2 can also be made of jacket walls with holes thereon so that the water or air jet can be provided through those holes opened on the jacket walls. Container 2 also has a lower grid 28*a* and an upper grid 28*b*. Preferably, grid 28*b* and 28*a* has a flat shape and horizontally placed inside container 2 at an upper and a lower position, respectively. A space defined by lower grid 28*a*, upper grid 28*b* and side walls of container 2 is used to accommodate a device to be treated. A tray 30 can be placed in the space and the device is placed in the tray 30 for cleaning and sterilizing. Stirrer 20 is located either in the space defined by upper wall 24, upper grid 28*b* and side walls of container 2, or in the space defined by sloped bottom wall 4, lower grid 28*a* and side walls of container 2, or in both. Container 2 further contains a vacuum port 32 located at the upper portion of container 2. Preferably, vacuum port 32 is located on the upper wall 24 of container 2 to avoid liquid in container 2 from entering vacuum port 32. A gas-permeable but microorganism-impermeable barrier 34 is secured to the vacuum port 32. Any conventional method can be used to seal barrier 34 into vacuum port 32 such as shown in FIG. 1*c*. In the connection shown in FIG. 1*c*, barrier 34 is placed in a barrier holder 34*a*. The barrier holder 34*a* is placed into a seat 34*b* formed between two end of two tubes. An O-ring 34*c* is provided around holder 34*a*. Thus, by clamping the two ends of the two tubes toward each other barrier 34 is secured and sealed. A valve 36 is provided at vacuum port 32. A vacuum pump 38 is connected to vacuum port 32 through valve 36. A detachable connector can be provided between valve 36 and vacuum pump 38.

Figure 1D:
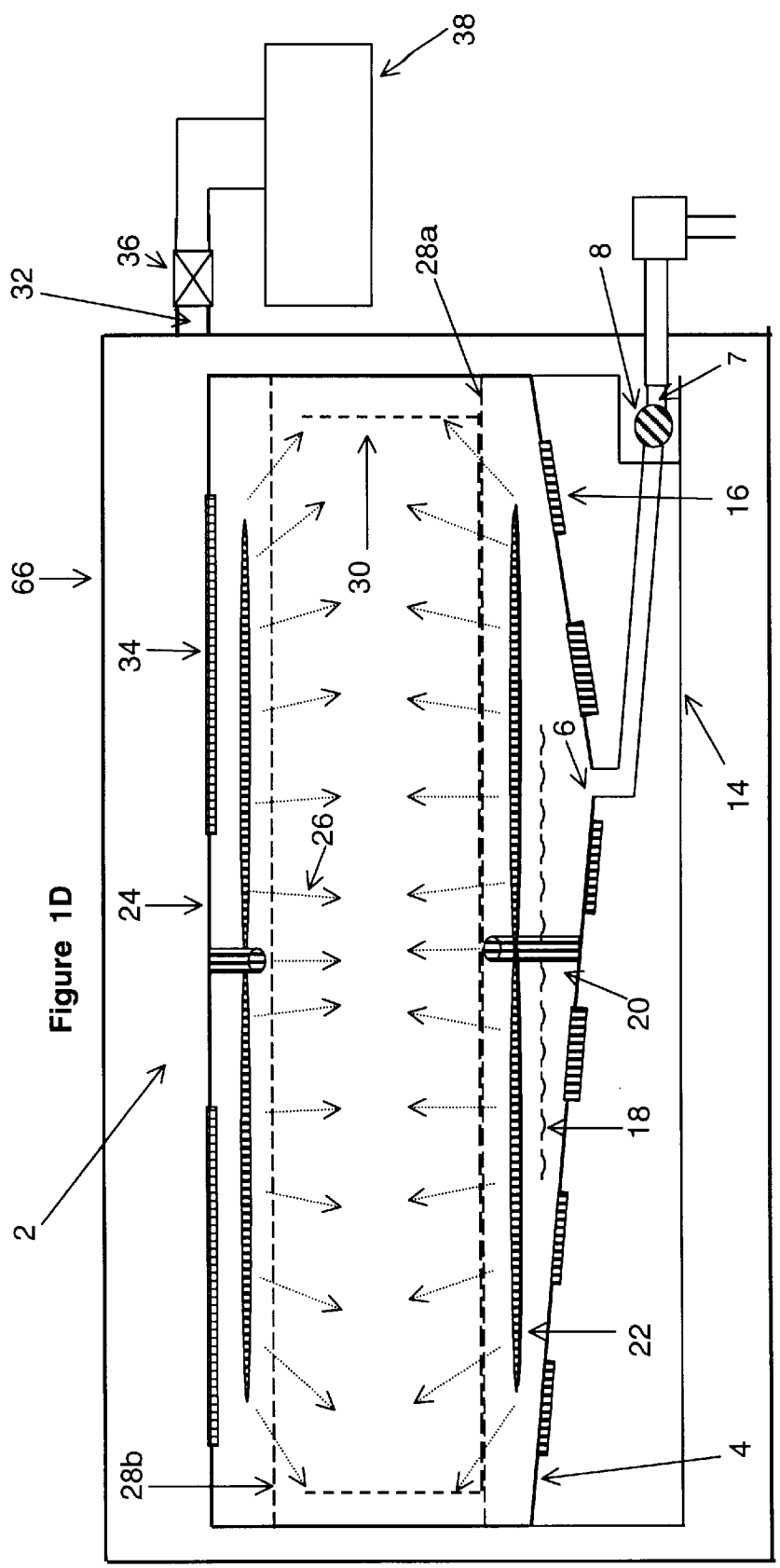
FIG. 1d is a schematic diagram of a container placed in a vacuum chamber used in a cleaning/sterilizing process of the present invention.

Container 2 of FIG. 1*a* can be placed into a vacuum chamber with slight modification. As shown in FIG. 1*d*, the same container 2 is used except that barrier 34 provided on upper wall 24 is not connected directly to the vacuum port 32 which is provided on the wall of a vacuum chamber 66.

Figure 1E:
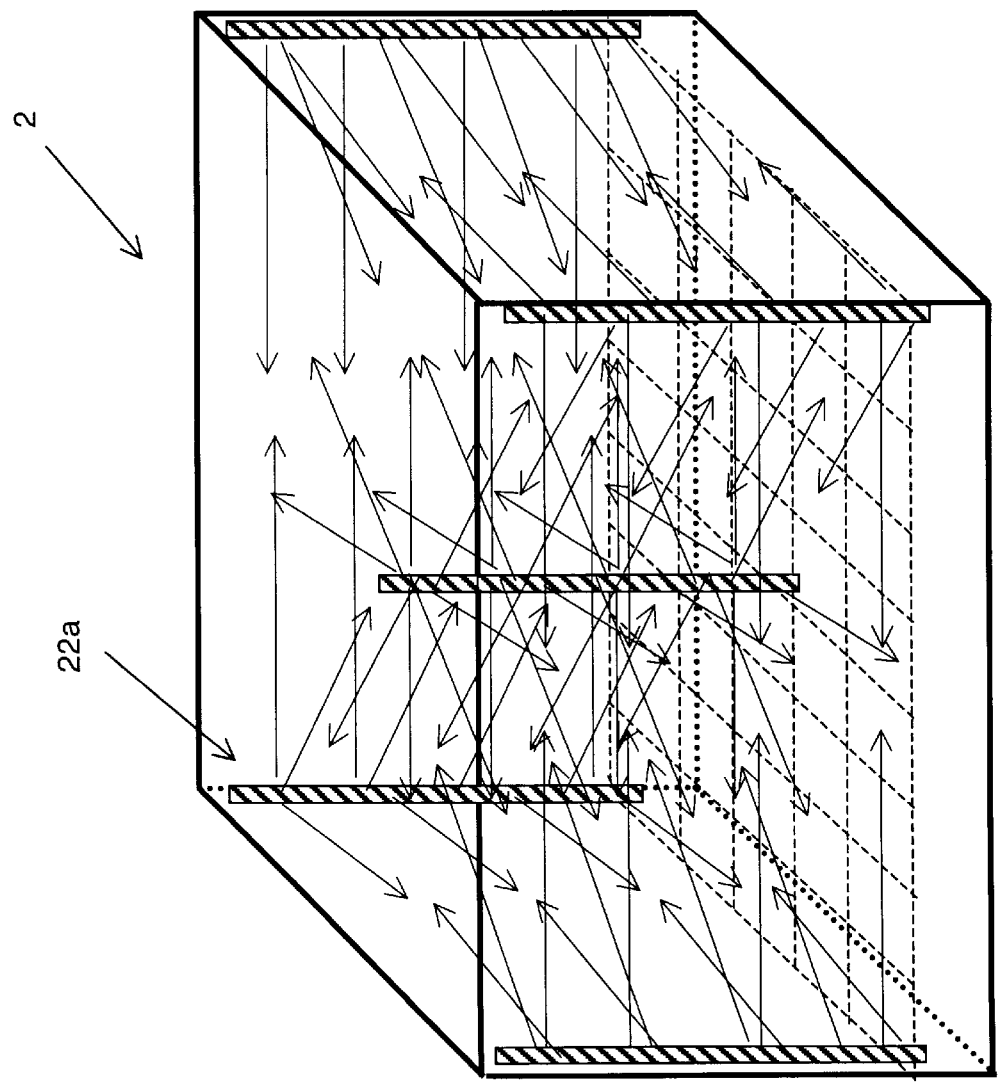
FIG. 1e is a schematic diagram of a container with fluid jet tubes.

FIG. 1*e* shows another way of providing a fluid jet in container 2. Instead of stirrers, several tubes 22*a* with small holes thereon are secured vertically in container 2 to provide a fluid jet such as a water jet or an air jet. Tube 22*a* can be positioned to provide an uniform spray, the orientation and shape of tube 22*a* can be determined according specific purposes. The rest parts can be the same as the container of FIG. 1*a*.

When using the above described container in the cleaning/sterilizing process of the present invention, one first places a device into the container 2. The device can be either placed on the lower grid 28*a* or placed in tray 30. Two grids 28*a* and 28*b* set the boundaries for the devices in the container and keep the device from being damaged by stirrer 20. The upper grid 28*b* is the fluid fill line to ensure all the devices are immersed in the fluid. Usually the device is first pre-cleaned in container 2 by a water jet to remove majority of soils, large particles, and other contaminates. During the pre-cleaning, the drain is usually kept open to remove the dirty water containing those particles and contaminates. Then the device is cleaned. In this step a cleaning solution is filled into container 2 through a liquid pump. The cleaning solution can be any conventional cleaning solution with enzyme and detergent solution preferred. During the cleaning step, stirrers, water jet, ultrasonics, or other suitable mechanism can be used to facilitate the cleaning process. When the cleaning is complete, the cleaning solution is drained through fluid port 6. A rinse solution is then introduced into container 2 through fluid port 6. The rinse solution can be water, alcohols, or other rinse liquid. The rinsing can be facilitated by stirrers, water jet, air bubbles, or other suitable mechanism. These steps can be repeated if desirable. After the rinsing step, air can be introduced through stirrer 20 to blow water off the device. Then a liquid sterilant is introduced into container 2 from the same fluid port, and the device is treated with the liquid sterilant for a desired time. Preferably, the liquid sterilant is a hydrogen peroxide solution or a peracetic acid solution. The main purpose of this step is to treat the device with the liquid sterilant and to provide right amount of the liquid sterilant. The sterilization is achieved mainly in next step. If necessary, excess of the liquid sterilant can be drained from container 2, and a predetermined amount of the liquid sterilant will be retained by the wells 18. This amount of liquid sterilant is determined based on the size of the load, the container, and the vacuum chamber. At this point, vacuum pump 38 is turned on and vacuum is applied to container 2 through vacuum port 32. In this step, the diffusion restricted environment method, the controlled pump down rate method, the two step pump down method discussed previously can be employed to achieve good sterilization results. When the sterilization is finished, container 2 is detached from the vacuum system, the device can be kept in container 2 and stored for future use. The sterility of the sterilized device is maintained in container 2 because container 2 is sealed except for the gas-permeable but microorganism-impermeable barrier 34. In one embodiment, valve 36 is closed when the pressure in container 2 is lower than atmospheric pressure and container 2 including the sterilized device is stored for use. This procedure provides a further means to check if the sterility of the device is well maintained in the container. If the container 2 is still under a pressure below the atmosphere before next use of the device, that means no air leaking into container 2 and, thus, no microorganism can enter container 2 during the storage. Any one of the above steps can be repeated if desirable. The sterilizing step can also be replaced with a disinfecting step by using a proper germicide.

Figure 2:
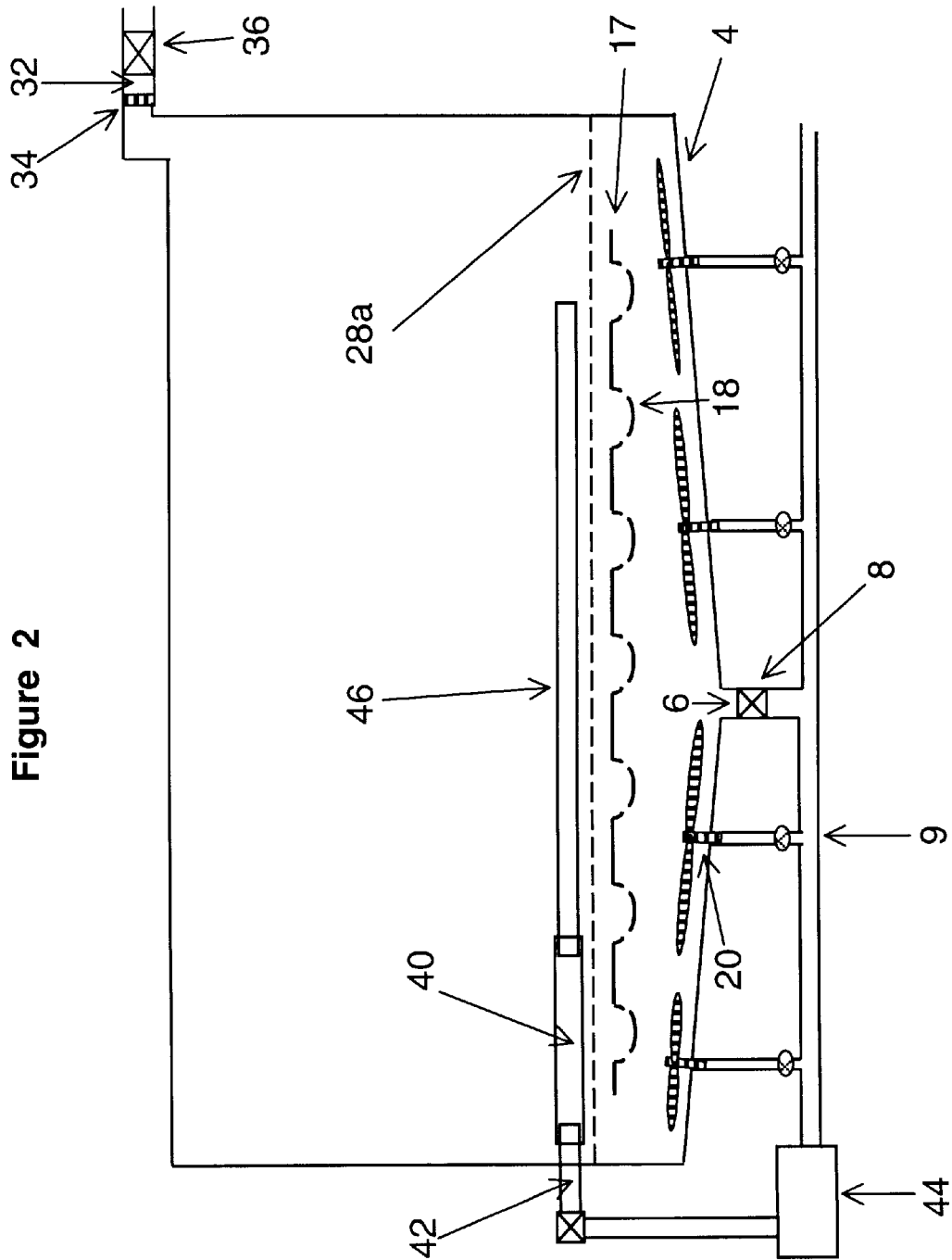
FIG. 2 is a schematic diagram of a container with an adaptor used in the cleaning/sterilizing process of the present invention.

FIG. 2 shows a container having adapters for connecting lumen devices. Similar to the container of FIG. 1*a*, container 2 shown in FIG. 2 has a sloped bottom wall 4 with a first fluid port 6 at the lowest point of the sloped bottom wall 4. Several stirrers are installed on the sloped bottom wall 4. A flat sheet metal grid 28*a* is horizontally located at the lower portion of container 2. Grid 28*a*, sloped bottom wall 4, and side walls of container 2 define a space accommodating stirrer 20 and wells 18 on plate 17. An adapter 40 is connected to a second fluid port 42 at one end and the other end for receiving a lumen device 46. A gas-tight seal, tight-fitting, or loose-fitting between adapter 40 and lumen device 46 can be formed. Adapter 40 can be any suitable conventional adapters used in the art. Preferably, the second fluid port 42 is located above grid 28*a*. Second fluid port 42 is also connected to a source 44 for generating a pressure difference between the two ends of a lumen device 46 which is connected with the second fluid port 42 through adapter 40. Source 44 can be a liquid pump for generating negative pressure, or a positive pressure. Lumen device 46 is placed on top of the grid 28a. Like the container shown in FIG. 1a, container 2 of FIG. 2 also has a vacuum port 32 with a gas-permeable but microorganism-impermeable barrier 34 and a valve 36. The barrier covers the vacuum port 32 and blocks passage for microorganism, valve 36 controls the opening and closing of the vacuum port 32. As shown, fluid port 6 and stirrers 20 are also connected with a tube 9 for draining fluid from container 2 or supplying fluid jet to stirrer 20. One end of tube 9 leads to a waste fluid collector, the other end is connected to pump 44.

Preferably, adaptor 40 comprises a cylindrical tubular body, a truncated cone, an opening, and textures on the outer surface of the truncated cone surrounding the opening, such as the adaptor shown in FIGS. 10–13.

Figure 3A:
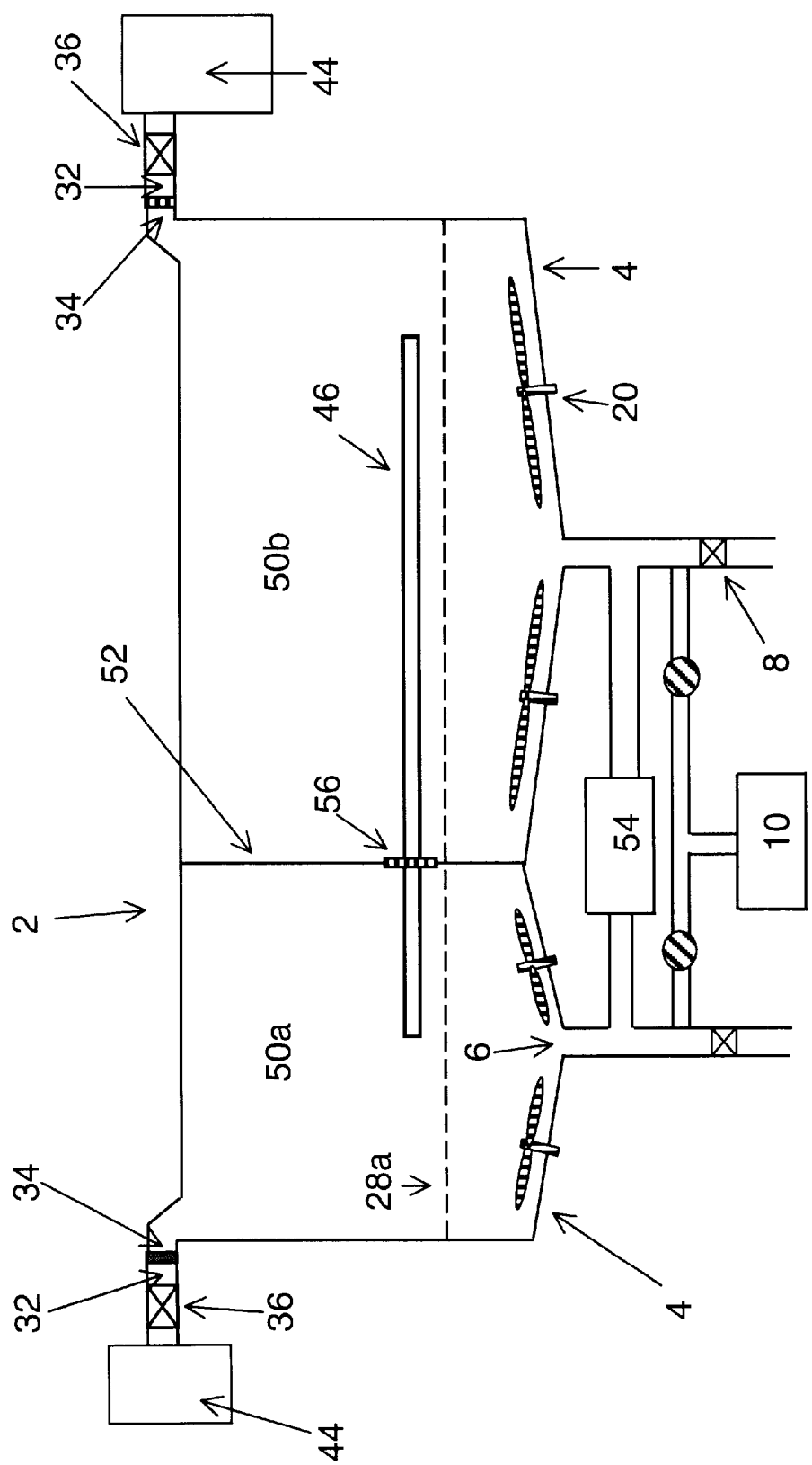
FIG. 3a is a schematic diagram of a container with an interface used in the cleaning/sterilizing process of the present invention.
Figure 3B:
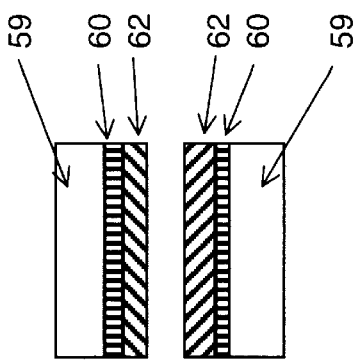

FIG. 3a shows a container 2 separated into a first enclosure 50a and a second enclosure 50b by an interface 52. As shown both enclosure 50a and 50b have a sloped bottom wall 4 with stirrer 20 secured thereon, a flat sheet grid 28a horizontally positioned at lower portion of enclosure 50a and 50b, and a fluid port 6, respectively. A pump 54 is provided between the two fluid ports 6. A vacuum port 32 is provided at the upper portion of enclosure 50a and 50b. A gas-permeable but microorganism-impermeable barrier 34 is connected to the vacuum port 32 to stop microorganism from entering enclosure 50a and 50b through vacuum port 32. Vacuum port 32 is also equipped with a valve 36 and a source 44 for generating pressure difference and providing vacuum. Preferably, source 44 is a vacuum pump for providing negative pressure or compressed air for providing positive pressure. Interface 52 has a controllable opening 56 (also referred as holder). Lumen device 46 is placed across opening 56 partly in enclosure 50a and partly in enclosure 50b. Opening 56 can be configured differently. For example, opening 56 can be made of a shutter 58 such as an iris diaphragm as shown in FIG. 3b, and the opening and closing of opening 56 can be controlled manually or automatically. In one embodiment, the blades of shutter 58 (eight blades are shown in FIG. 3b), can be divided into two groups. For example, each group contains four blades not next to each other. These two groups of blades are controlled separately by a controller so that while one group is in the close position holding the device to be sterilized the other group is in open position allowing the sterilant to sterilize the area occluded by the blades when the blades are in closed position. Another example of shutter 58 is the Syntron Iris Flow Control Valve (by FMC Corporation) or the Iris diaphragm valves (Kemutec Inc.) as shown in FIG. 3c. Briefly, Iris valve 58a has a cylindrical sleeve 90 with two retaining rings 92 located at two ends of the cylindrical sleeve 90. Sleeve 90 is made of Teflon or other suitable plastic or rubber material. When in use, a lumen device is inserted through an aperture 94 of cylindrical sleeve 90. A first retaining ring 92 is secured and sealed to opening 56, a second retaining ring 92 is free to rotate and coupled to interface 52 through a conventional mechanical mechanism (not shown) so that the turning of the second retaining ring 92 can be controlled mechanically or electronically from outside container 2. By rotating the retaining rings 92 relative to each other, the diameter of aperture 94 of the cylindrical sleeve 90 can be increased or reduced, or totally shut off. If desirable, more than one shutter can be provided in the interface 52.

Figure 3D:
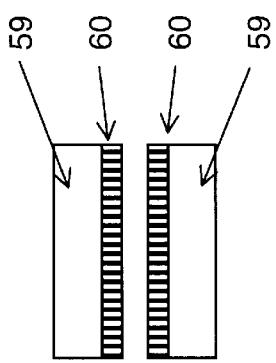
Figure 3F:
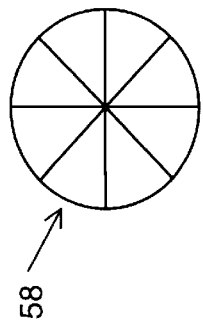
Figure 3C:
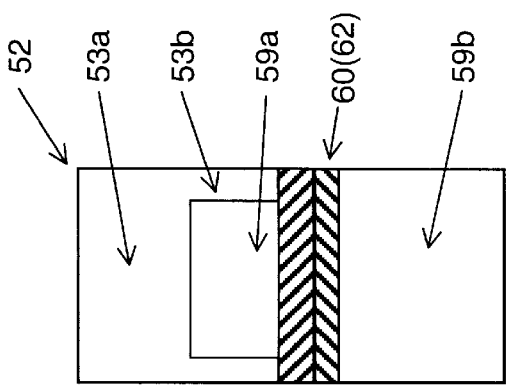
Figure 3E:
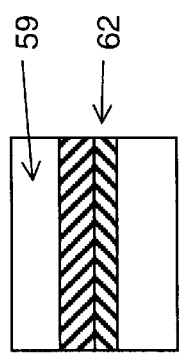

Opening 56 also can be a slot or a gap defined by two plates 59 as shown in FIGS. 3d and 3e. The contact edges or surfaces of plate 59, which form the slot and hold the lumen device 46, are equipped with a layer of expandable material 60 such as silicon, or a layer of compressible material 62.

Figure 3G:
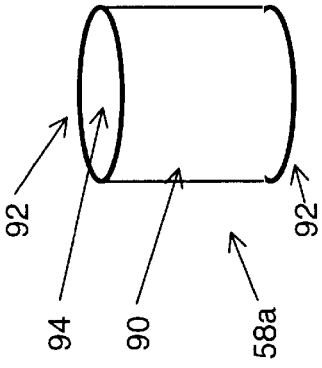

The closing, and thus seal around lumen device 46, of the slot can be done either by moving plate 59 or expanding expandable material 60. With a two-plate opening 56, more than one lumen device can be placed across the opening 56. When expandable or inflatable material is used on plate 59, an expansion fluid source can be provided to plate 59 to expand the expandable material 60. In one embodiment, a layer of compressible material 62 is provided on top of the layer of expandable material 60 as shown in FIG. 3f. In another embodiment, the opening 56 is formed by an upper plate 59a and a lower plate 59b as shown in FIG. 3g. The lower plate 59b has a rectangular shape with a bottom edge and two side edges being secured and sealed to the bottom wall and two side walls of container 2, respectively. The upper plate 59a also has a rectangular shape and its upper portion is movably inserted into a housing 53a. Housing 53a forms the upper portion of interface 52. A portion of housing 53a extends along two side walls of container 2 to the upper edge (or contact surface) of lower plate 59b, forming two rails 53b for receiving the two side edges of upper plate 59a and guiding the movement of the upper plate 59a. There provided a seal between the upper plate 59a and the housing 53a and rail 53b. For example, an O-ring can be used in housing 53a and rail 53b to seal the upper plate 59a. The upper edge of the lower plate 59b and the lower edge of the upper plate 59a are provided with a layer of compressible or expandable material. The movement of the upper plate 59a can be controlled by any suitable conventional method, mechanically or electrically, form the outside of container 2. Many different configurations and structures can be adopted for the opening 56. For example, the contact surface of opening 56 can be made of an uneven surface so that, when opening 56 is closed around a lumen device, the uneven surface will provide passage to allow both liquid and gas to pass therethrough while holding the lumen device. Thus, the occlusion area on the lumen device surface can be significantly reduced. The uneven surface may have textures, projections, sharp edges, or sharp points thereon.

In another embodiment, opening 56 is an aperture equipped with a layer of porous material or with a layer of expandable material and a layer of porous material on top of the expandable material. Opening 56 also can be made of an aperture of suitable shape, such as cylindrical or conical, lined with porous material or textures. A shutter can be secured to the aperture providing a steady holding of the lumen device 46 with minimal contact area or occlusion area.

Figure 4:
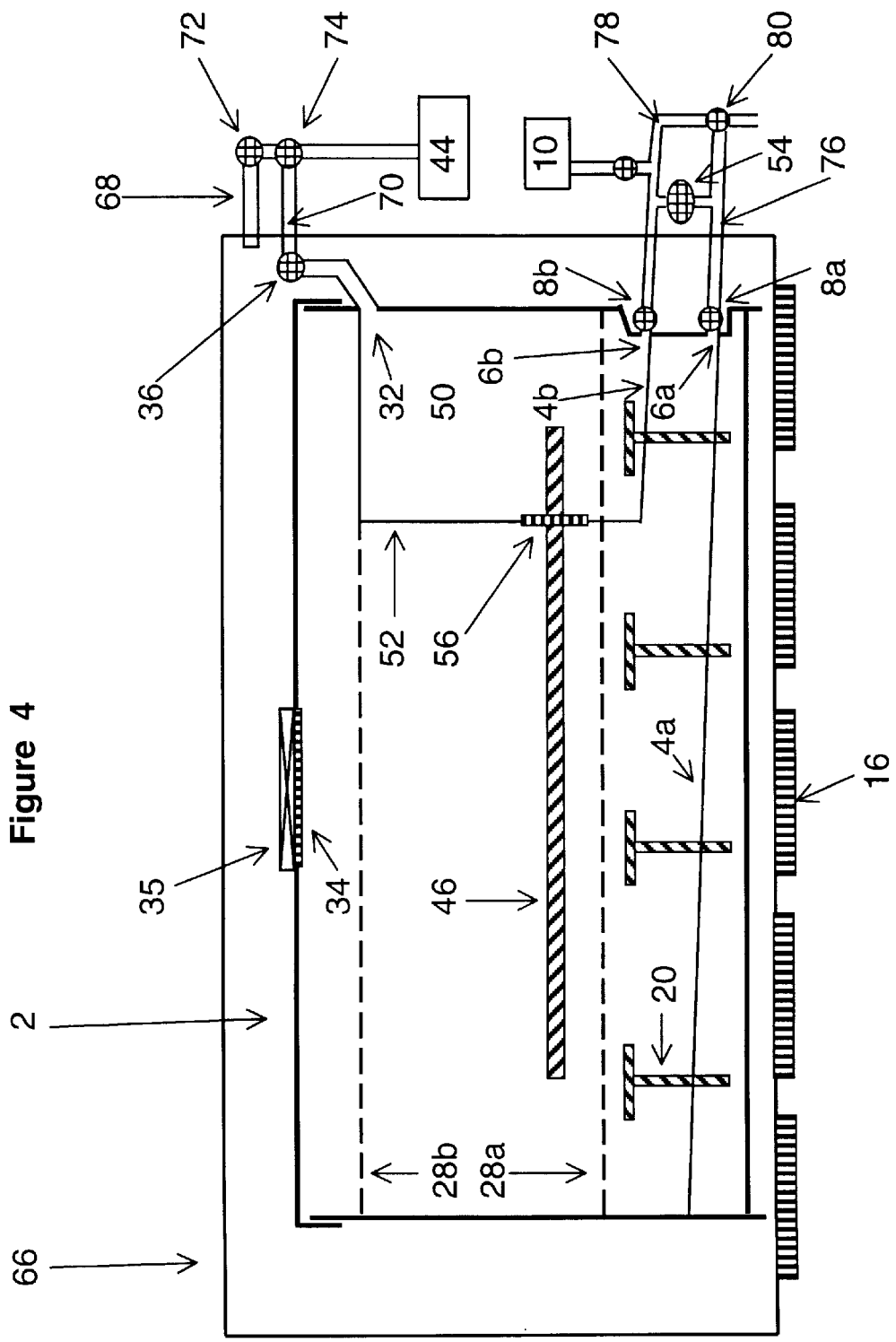
FIG. 4 is a schematic diagram of a container placed in a vacuum chamber used in the process of the present invention.

FIG. 4 shows a container 2 with an enclose 50 separated by an interface 52. In this embodiment, the container 2 with the enclosure 50 is placed inside and coupled to vacuum chamber 66. Vacuum chamber 66 has a first vacuum port 68 which is in gas communication with container 2 through a gas-permeable but microorganism-impermeable membrane 34 installed on the upper wall of container 2, and which is preferably located at the upper portion of a side wall of vacuum chamber 66. A valve 35 is provided above membrane 34 to control the opening and closing of gas communication of container 2 with outside through membrane 34. Vacuum chamber 66 also has a second vacuum port 70 connecting to a vacuum port 32 of the enclosure 50 through a valve 36. Preferably, the second vacuum port 70 also located at the upper portion of the side wall of the vacuum chamber and near the first vacuum port 68. Valve 36 is preferably located outside the enclosure 50 and inside the vacuum chamber 66. A detachable connector (not shown) is preferably provided between valve 36 and second vacuum port 70 for attaching valve 36 to and detaching valve 36 from the second vacuum port 70. The first and second vacuum ports 68 and 70 are connected to each other outside the vacuum chamber 66. A valve 72 is provided at first vacuum port 68 to control flow through the first vacuum port 68. A valve 74 can also be provided at the common inlet of the first and second vacuum ports 68 and 70. A source 44 for generating pressure difference between the two ends of the lumen device 46 is provided at the common inlet of first and second vacuum ports 68 and 70. Preferably, source 44 is a vacuum pump for generating a negative pressure or compressed air for generating a positive pressure. Vacuum chamber 66 also has a first fluid port 76 connecting to a fluid port 6a of the container 2 through a valve 8a, and a second fluid port 78 connecting to a fluid port 6b of the enclosure 50 through a valve 8b. The first and second fluid ports 76 and 78 are located at the lower portion of a side wall of the vacuum chamber 66 and close to each other. The fluid port 6a is located at the lowest point of a sloped bottom wall 4a of the container 2. In this embodiment, the fluid port 6a is located at one lower corner of the container 2. The fluid port 6b is located at the lowest point of a sloped bottom wall 4b of the enclosure 50. In this embodiment, the fluid port 6b is located at one lower corner of the enclosure 50. A detachable connector can be provided for connecting valve 8a and 8b to first and second fluid port 76 and 78, respectively. Outside the vacuum chamber 66, first and second fluid ports 76 and 78 are connected to each other forming a common fluid inlet which is provided with a valve 80. A liquid pump 54 is also provided between the first and second fluid ports 76 and 78 to circulate a fluid between the container 2 and the enclosure 50. The container 2 has a lower grid 28a and an upper grid 28b. Preferably, the lower grid 28a and the upper grid 28b are a flat metal sheet and horizontally positioned at the lower and the upper portion of the container 2, respectively. Stirrers 20 are located below the lower grid 28a. Interface 52 has an opening (or holder) 56 for holding a lumen device 46. The opening 56 can be configured in many different ways such as those described with FIGS. 3b–3f. On the bottom wall of vacuum chamber 66, a plurality of transducer 16 is provided to generate ultrasonics. Accordingly, the space between outer surface of the bottom of container 2 and the inner surface of the bottom wall of vacuum chamber 66 is filled with water or other suitable liquids providing a medium for the ultrasonics.

In using the apparatus with containers and enclosures separated by an interface in the cleaning/sterilizing or cleaning/disinfecting process of the present invention, a lumen device is placed into the container 2 and the enclosure 50 across the interface 52. The opening 56 of the interface 52 is then closed manually or automatically, if an openable and closeable opening 56 is used. Thus, opening 56 forms a seal around the lumen device. The extent of the sealing can be controlled through different degree of tightening of the opening 56 around the lumen device 46 for different purposes. As defined previously, three types of seal can be made between the opening 56 and the lumen device 46, gas-tight seal, loose-fitting seal and tight-fitting seal. If maximum pressure is intended a gas-tight seal should be used in this case the container 2 is substantially totally sealed from the enclosure 50, neither gas nor liquid can flow through the space between the opening 56 and the lumen device 46. Under many situations such a gas-tight seal is not necessary. In this case, a tight-fitting seal can be used so that a portion of fluid in the system can flow or diffuse through the space between the opening 56 and the lumen device 46, but a large portion of the fluid flows through the lumen of the lumen device 46, and the lumen device 46 is still held in position by the opening 56 during agitation. Loose-fitting will provide a opportunity to clean/sterilize the outer surface area of the lumen device 46 which is otherwise obscured by the opening 56.

A cleaning solution is then introduced into the container 2 and the enclosure 50 through fluid port 6a and 6b, respectively. The liquid level in the container 2 and the enclosure 50 is preferably not higher than the position of the vacuum port 32. A stirrer, a water jet or an air jet can be used to facilitate the cleaning of the outer surface of the lumen device 46. The cleaning solution is also circulated between container 2 and enclosure 50 through the lumen of the lumen device 46. There are at least two ways to make the circulation. One method is to apply vacuum to the enclosure 50 through second vacuum port 70 of vacuum chamber 66 and vacuum port 32 of the enclosure 50 while keeping vacuum chamber 66 and container 2 at atmospheric pressure or any pressure higher than that of the enclosure 50. This can be done similarly when vacuum chamber 66 is not used. The cleaning fluid then flows from the container 2 into the enclosure 50 through the lumen device 46. The liquid pump 54 circulates the cleaning fluid back to the container 2. The opening 56 and the stirrer 20 can be controlled by the electronic signals from the system. Air bubbles generated from air pump 10 can be introduced at this stage to enhance the scrubbing action during cleaning. Thus, both the outer surface and the inner surface of the lumen device 46 can be cleaned at the same time. Vacuum can be applied to container 2 to generate a pressure in the container 2 lower than that of the enclosure 50. Forced air also can be used to push liquid through the lumen. If desired, the interior and the exterior of the lumen device can be cleaned separately. The cleaning fluid can be removed from the container 2 and enclosure 50 through the fluid port 6a and 6b on the sloped bottom wall 4a and 4b. The cleaning fluid in the lumen device 46 can be removed either with vacuum or forced-air.

The rinsing with water and the treatment with liquid sterilant can be conducted similarly. When the treatment with a liquid sterilant is complete, the liquid sterilant is drained and a predetermined amount of the liquid sterilant can be retained in the wells. Then vacuum is applied to chamber 66 and container 2 either through vacuum port 68 or 70, or both in a manner described earlier. At least in certain stage, the vacuum should be high enough (or the pressure low enough) to vaporize the remaining sterilant in container 2 to sterilize and dry the device simultaneously. A plasma can be used as an option to enhance the efficacy and/or to remove the sterilant residual. After the sterilization is completed, the chamber is vented and the container is ready to be retrieved from the chamber. If desired, valve 35 can be closed at any pressure below the atmospheric pressure and the sterilized device is kept in container 2 under a subatmospheric pressure. This may serve as an indication of a well maintained sterility, i.e. if the vacuum still exists when container is opened after a period of time of storage that indicates the sterility of the sterilized device is well kept. The pressure can be monitored and controlled by the pressure sensor on the vacuum chamber 66 or in container 2.

Figure 5A:
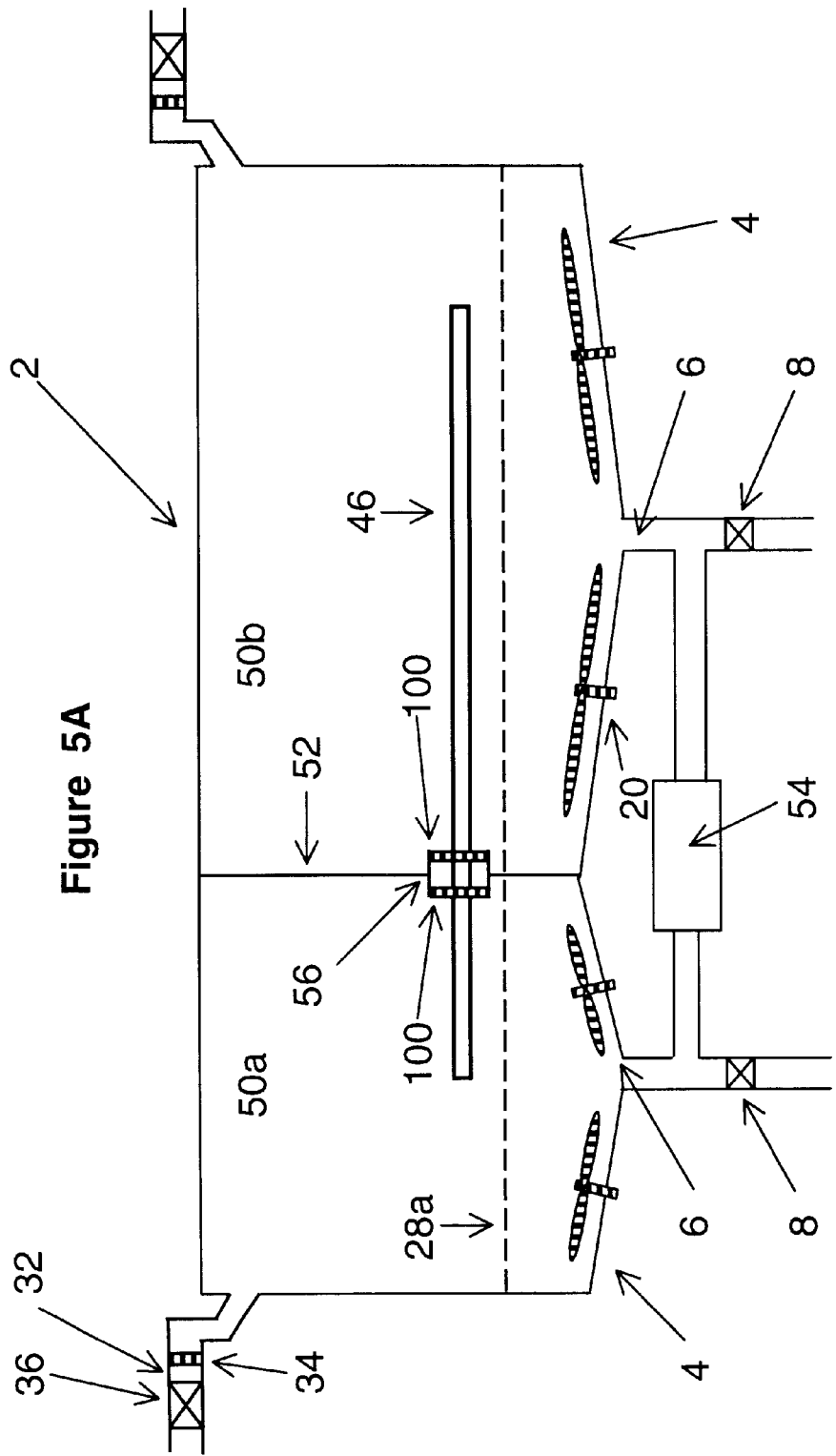
FIG. 5a is a schematic diagram of a container having two holders in an interface.

FIG. 5a shows a container very similar to that shown in FIG. 3a except that two holders 100 are used in opening 56 of interface 52. As shown in FIGS. 5a and 5b, the two holders 100 are secured to opening 56 along lumen device 46 or the passage of opening 56. Each holder 100 is sealed to opening 56 in any suitable conventional manner and each holder 100 is independently controllable. Holder 100 can be a shutter as the shutter described with FIGS. 3b and 3c, or made of two plates as described with FIGS. 3d–3g. FIG. 5b shows two holders 100 of shutter type holding a lumen device 46. During cleaning or sterilizing operation, a first holder 100 is first closed and a second holder 100 is opened, then the first holder is opened and the second holder 100 is closed. Thus, enclosures 50a and 50b are always separated or insulated from each other through the engagement of one holder 100 with the device 46 and, in the meantime, the two contact surface areas of the device 46 occluded by the two holders 100 are exposed alternately.

Figure 5C:
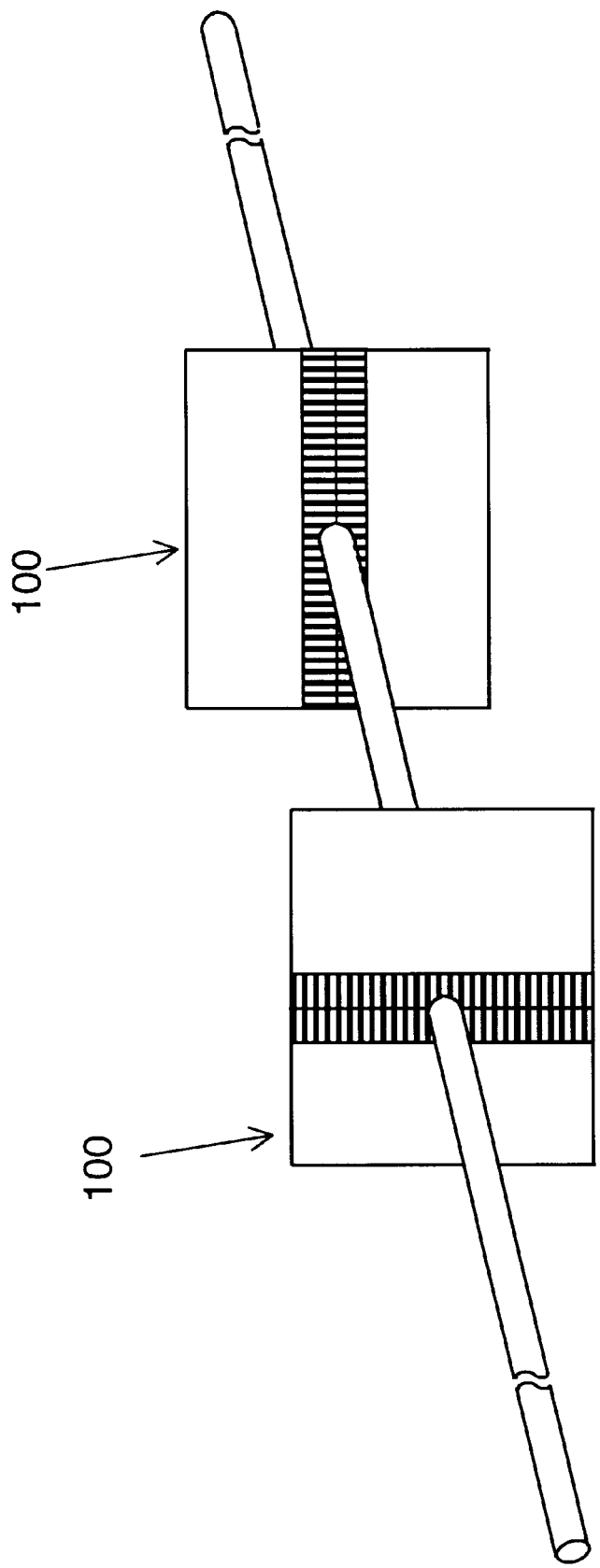

FIG. 5c shows two holders 100 of plate type holding a lumen device 46. Each of holders 100 can be constructed in the way as described previously with FIGS. 3d–3g. Preferably, the gap (the opening for passing the lumen device) formed between the two plates of one holder 100 forms an angle with that of the other holder 100 of the two holder structure. Preferably, the angle is 90 degree as shown in FIG. 5c. The two holders 100 are preferably positioned close enough so that when the expandable material 60 lined in the gap (opening) is expanded, the expandable material 60 will also expand outwardly away from the two plates and become in contact with the other holder 100, thus help seal the gap of the other holder 100. This configuration provides an advantage that no complete seal is needed for a single holder, yet a good seal such as a gas-tight seal can be achieved when two such holders are combined. It has been noted by the applicants that, when a cylindrical lumen device is placed across the gap between the two plates of holder 100, areas on the outer surface of the lumen device, where the diameter of the cylindrical lumen device is parallel to the gap, are more difficult to seal because the expandable material 60 has to expand extra distance to cover those areas. By providing two closely positioned holders 100 with the two gaps forming an angle, the above mentioned areas in each of the two holders can be sealed by the other holder. Therefore, the requirement to the expandable material can be lowered without sacrificing the sealing characteristics.

Figure 5D:
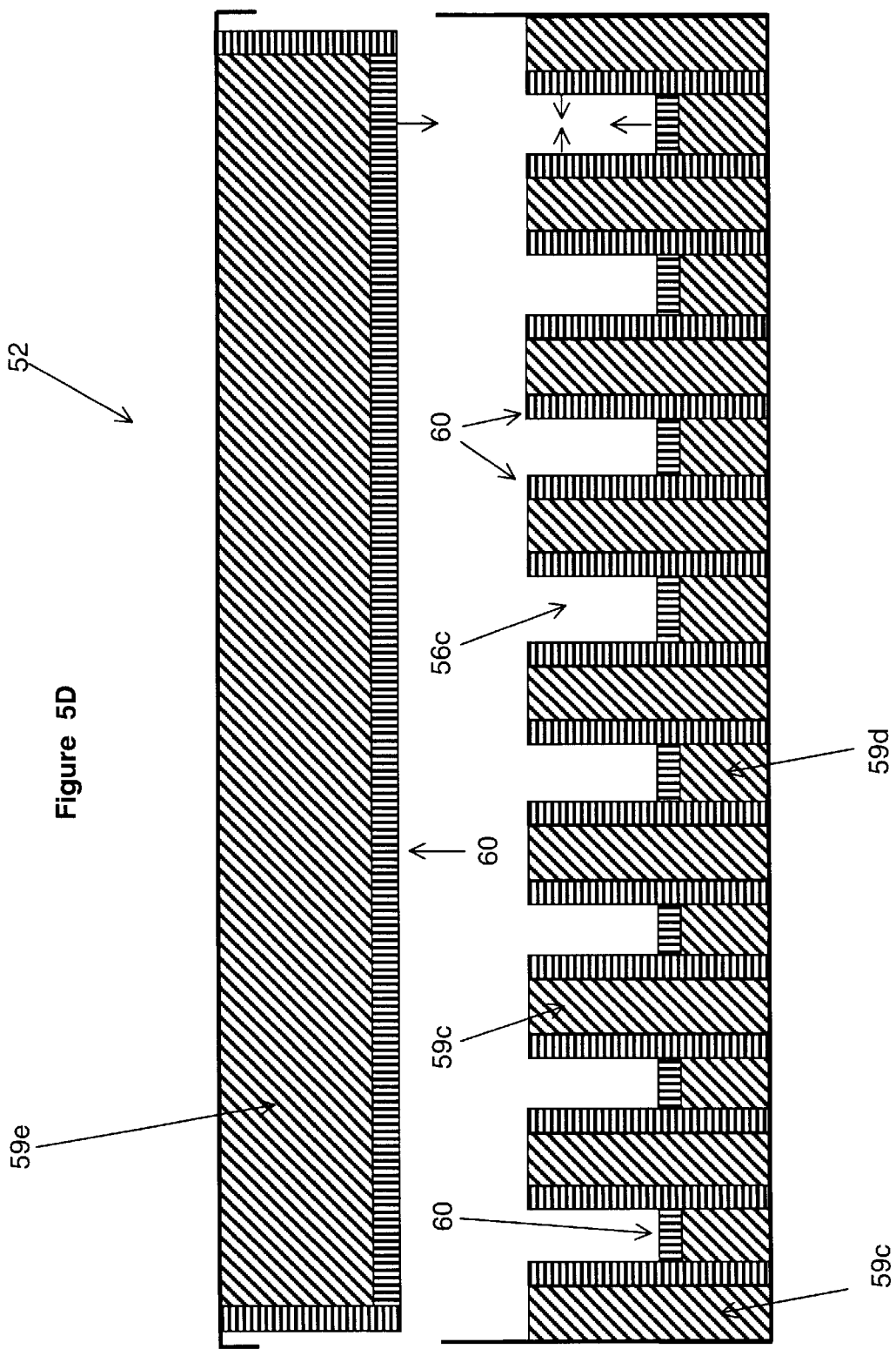
FIG. 5d is a schematic diagram of an interface of a container with multiple openings.

FIG. 5d shows another embodiment of an interface of the present invention. In this embodiment, the interface 52 contains multiple openings 56c. This interface 52 may have three parts. A first plate 59c has a plurality of openings 56c thereon. The cross section of the opening 56c as viewed from a direction perpendicular to the surface of plate 59c has an elongate shape with its longitudinal axis extending along a substantially vertical direction. Other orientation also can be adopted. Preferably, opening 56c has a rectangular cross section. The upper side of the openings 56c can be made open for easy access to a lumen device. The contact surface of opening 56c is provided with a layer of expandable material 60. A second plate 59d is positioned beside the first plate 59c in parallel. Plate 59d can be secured and sealed to the bottom and side walls of container 2 with its upper edge or surface equipped with a layer of expandable material 60. A third plate 59e is located above and aligned with second plate 59d. The third plate can be made a part of the lid for container 2. The lower edge of plate 59e and the upper edge of plate 59d form a gap for passing a lumen device. The edges of the third plate is also provided with a layer of expandable or other sealing material 60. Preferably, the second plate 59d and the third plate 59e lie in one vertical plane, and the first plate 59c lies in another vertical plane parallel to that containing second plate 59d and third plate 59e. Preferably, the gap formed between plate 59d and 59e forms an angle with openings 56c, more preferably the angle is a right angle. In one preferred embodiment, the gap between second plate 59d and third plate 59e has a horizontal orientation, and the openings 56c have a vertical orientation. The distance between the first plate 59c and the second and third plate 59d and 59e can be adjusted depending on intended purpose. Preferably, they are closely positioned relative to each other so that when the expandable material 60 on one plate is expanded, it will become in contact with the other plate to further facilitate seal around the lumen device passing both the gap between plate 59d and 59e and the opening 56c of plate 59c. Preferably, the dimension and the expandable material layer of opening 56c is determined to allow the opening 56c to be closed and sealed when the expandable material is expanded even no lumen device is placed through the opening.

Figure 6:
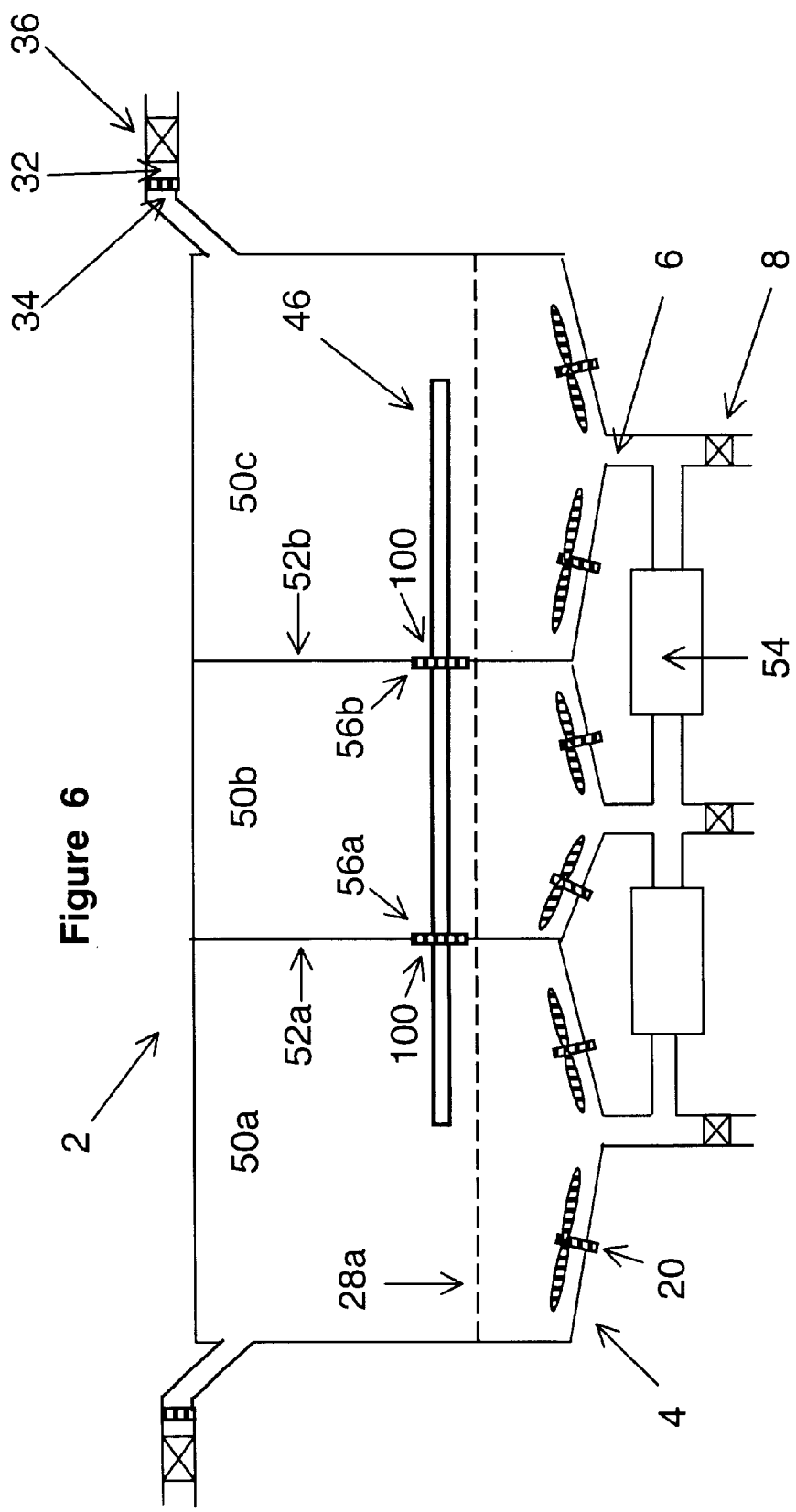
FIG. 6 is a schematic diagram of a container separated into three enclosures by two interfaces according to the present invention.
Figure 8A:
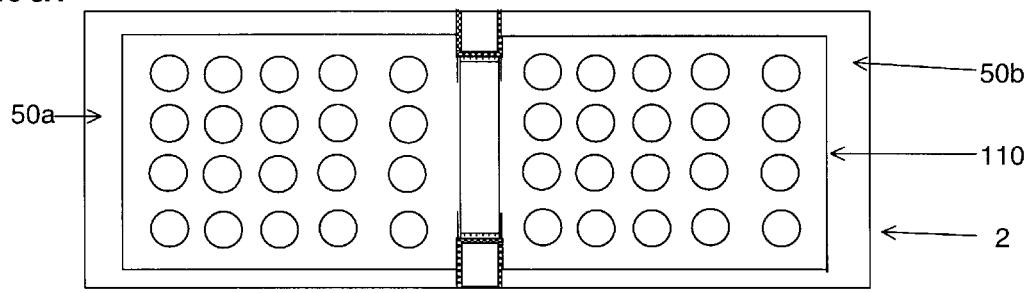
Figure 8B:
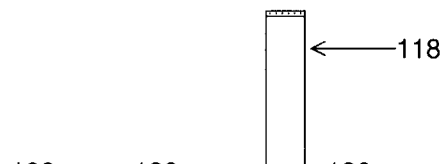
Figure 8C:
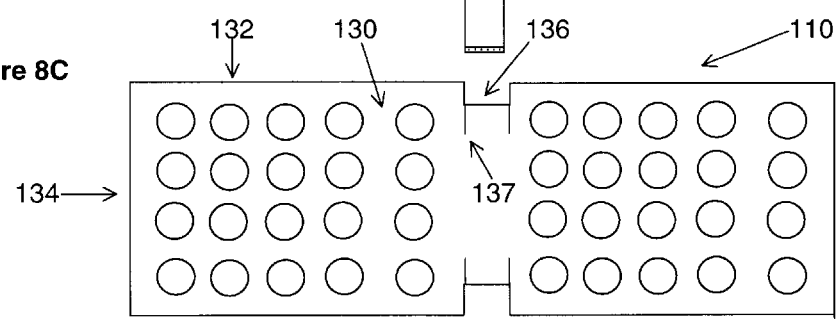
Figure 8D:
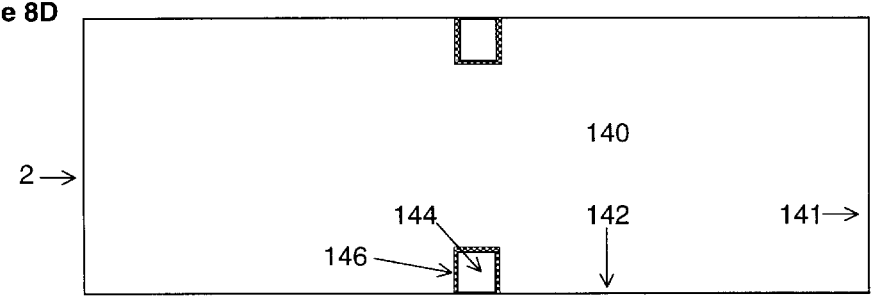
FIG. 8d is a top view of the container of FIG. 7a without the tray and the interface.

FIG. 6 shows a container 2 has three enclosures 50a, 50b, and 50c separated by two interfaces 52a and 52b, respectively. Enclosure 50b is located in between and shares interfaces 52a and 52b with enclosure 50a and 50c. Other parts of the container 2 of FIG. 6 are similar to those of the container shown in FIG. 3a, and they are indicated by same numerical references. Two openings 56a and 56b are located in interface 52a and 52b, respectively. Two holders 100 are also located in interface 52a and 52b. Opening 56a and 56b can be of any form as discussed previously. In practice of the process of the present invention, a lumen device 46 is placed across both opening 56a and opening 56b with one end located in enclosure 50a and the other end in enclosure 50c. The advantage of the configuration is to help obtain a large pressure drop between the two ends of the device 46. Under certain circumstances, the seal between the opening and the lumen device may be not gas-tight, thus it is difficult to keep a large pressure drop at the two sides of the interface with such a seal. By adding one intermediate enclosure 50b, the pressure drop across each interface 52a and 52b can be kept at a relative low level, yet the total pressure between the two ends of the device 46 or, in other words, between enclosure 50a and enclosure 50c can be still large enough to generate desired flow rate through the lumen of the lumen device 46. If desired, one interface 52a or 52b can be removed or opened, and in those cases the container 2 can be operated just like that of FIG. 3a.

FIG. 7a shows a container 2 separated into an enclosure 50a and an enclosure 50b by an interface 52 similar to the container of FIG. 3a except that a tray 110 is placed across interface 52 and located in both enclosure 50a and enclosure 50b. The tray 110 shown in FIG. 7a has a rectangular shape with four side walls perpendicular to a bottom wall defining a space for receiving a lumen device 46. The side and bottom walls have open holes thereon. As shown in FIG. 7b, interface 52 can be configured to have two parts. The first part forms a tray seat 112 extending along an interior periphery of container 2. Tray seat 112 has a first edge secured and sealed to the interior periphery of container 2 and a second edge 114 shaped to receive tray 110. Edge 114 has a bottom portion and two side portions defining an open rectangular cross section. On top of edge 114 is a sealing layer 116 made of expandable, compressible, or other suitable material. When tray 110 is placed into container 2, an exterior periphery of tray 110 will seat on edge 114 and layer 116. The second part of interface 52 can be a removable plate 118 having an edge 120 shaped to fit the shape of an interior periphery of tray 110. On top of edge 120 is a sealing layer 122 made of expandable, compressible, or other suitable material. Plate 118 is inserted into tray 110 along an interior periphery of tray 110. A guide rail can be provided with tray 110 to guide plate 118 moving along an predetermined interior periphery. Different shapes can be used for edge 114 of seat 112 and edge 120 of plate 118, as long as the shape matches that of the exterior and interior periphery of tray 110. For example, in one embodiment, the open rectangular formed by edge 114 and edge 120 shown in FIG. 7*b* is modified by making the upper edge longer than the bottom edge of the open rectangular and tray 110 has a corresponding shape. This configuration makes it easier to the plate 118 down into tray 110 and seal it. Plate 118 can further include an opening 56 of any kind as discussed previously with FIGS. 3*b*–3*g*. Opening 56 can be located in plate 118 or on edge 120 facing the bottom of tray 110 where lumen device is placed. In one embodiment, a layer of expandable, compressible, or other suitable sealing material is also provided with tray 110 along the interior periphery where plate 118 is inserted. FIG. 7*c* shows another embodiment in which tray 110 has a partition 111 therein. Partition 111 can be made as part of the tray 110. Upper edge 111*a* of partition 111 has a layer of expandable, compressible, or other suitable sealing material. Partition 111 is aligned with plate 118 so that when plate 118 is inserted into tray 110 seal can achieved between upper edge 111*a* of partition 111 and lower edge of plate 118, and a lumen device can be placed through the gap or opening 56 formed between upper edge 111*a* of partition 111 and lower edge of plate 118. In one embodiment, in the contact area between tray 110 and interface 52 (or plate 112 and 118), a portion of side and bottom walls of tray 110 is removed so that in those portion the sealing layer 116 of tray seat 112 and the sealing layer 122 of plate 118 of the interface 52 are in direct contact. Plate 118 can be secured to a lid or cover 119 for container 2 and, a portion of the lower surface of the cover 119 is provided with a layer of expandable, compressible, or other suitable sealing material to seal the upper edge of the tray 110 and the container 2 as shown in FIG. 7*c*.

When exposed to a pressure difference between enclosure 50*a* and 50*b*, tray 110 may be forced to move from high pressure side to low pressure side. In order to prevent this from happening, a stopper mechanism is provided. In one embodiment as shown in FIGS. 8*a*–8*d* which are top views of container 2 and tray 110, tray 110 has a rectangular bottom wall 130 with two side walls 132 along two longer edges of bottom wall 130 and two side walls 134 along two shorter edges of bottom wall 130. There is an indentation on each side wall 132 extending along the entire height of side wall 132 and substantially perpendicular to bottom wall 130. Container 2 also has a rectangular bottom wall 140 with two side walls 142 along the two longer edges of bottom wall 140 and two side walls 141 along two shorter edges of bottom wall 140. There is a projection 144 on each side wall 142 extending along the entire height of side wall 142 and perpendicular to bottom wall 140. The surface of projection 144 is covered with a layer of expandable, compressible, or other suitable sealing material 146. The projection 144 has a shape matching that of the indentation 136. When tray 110 is placed into container 2, indentation 136 will engage with projection 146 so as to hold tray 110 in position. A tray seat 112 with a layer of sealing material on its upper surface is provided on bottom wall 140 of container 2 extending between two projections 146. Tray 110 also has two edges 137 on each side wall 132 extending inwardly from indentation 136. A removable plate 118 with a layer of sealing material on its contact edge is inserted into tray 110 through a rail defined by extruding edge 137. In another embodiment, each side wall 141 is provided with a stopper, such as an extrusion, to confine the movement of tray 110 along a direction perpendicular to interface 52.

Figure 9:
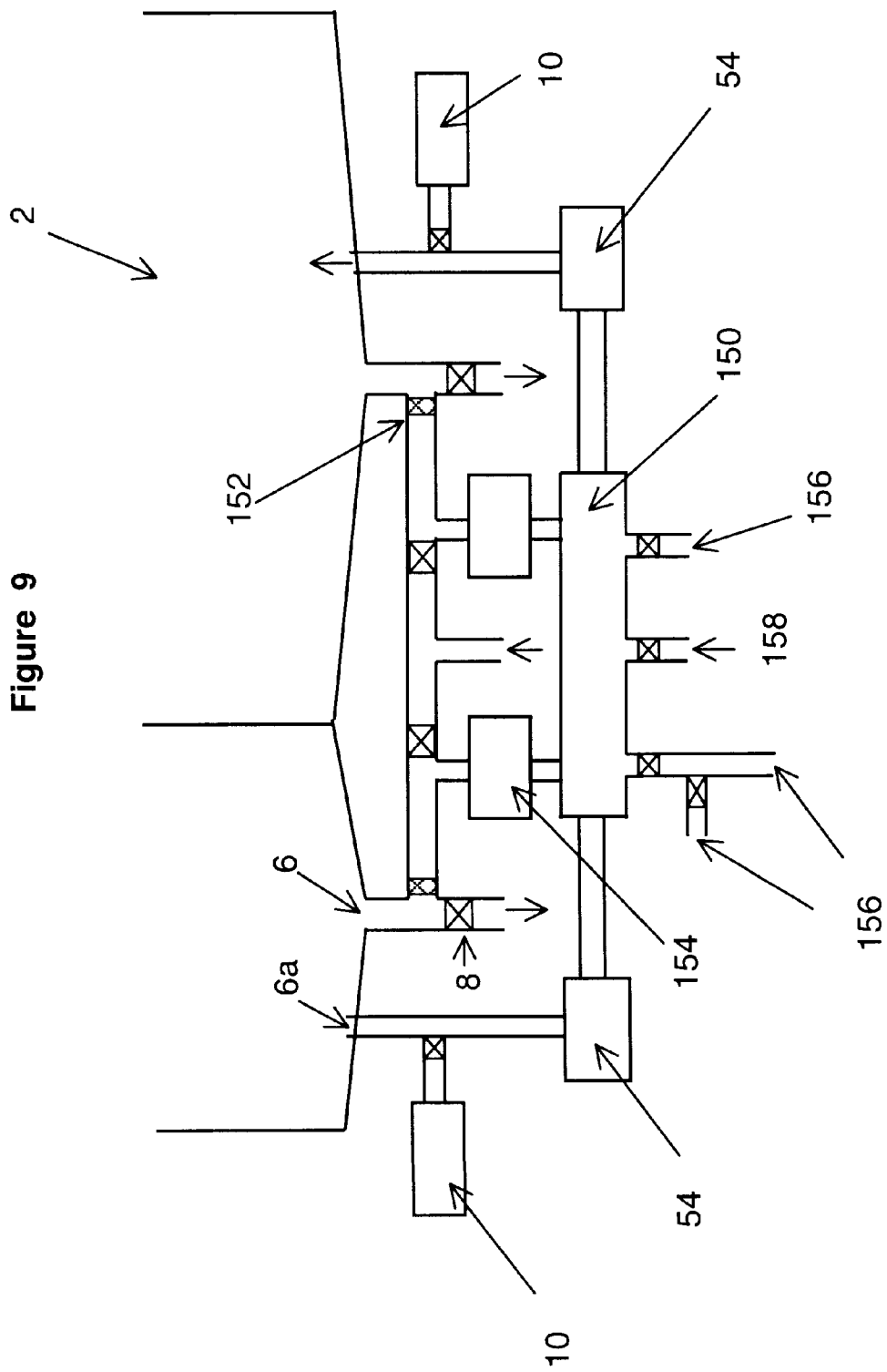
FIG. 9 is a schematic diagram showing a recycle system for processing liquid.

FIG. 9 shows a recycling system which can be incorporated into any container systems used in the present invention. In this system, used liquid in a cleaning/sterilizing process is drained or pumped to a reservoir 150 through a filter 152. A pump 154 can be provided between reservoir 150 and fluid port 6 to help drain the used liquid into reservoir 150. The filtered liquid in reservoir 150 can be then cycled back to container 2 through a fluid port 6*a*. If necessary, filter 152 can be cleaned by back flash. Reservoir 150 is also equipped with several inlets 156 for water, cleaning chemical, and sterilant, respectively, and a drain 158.

Figure 10:
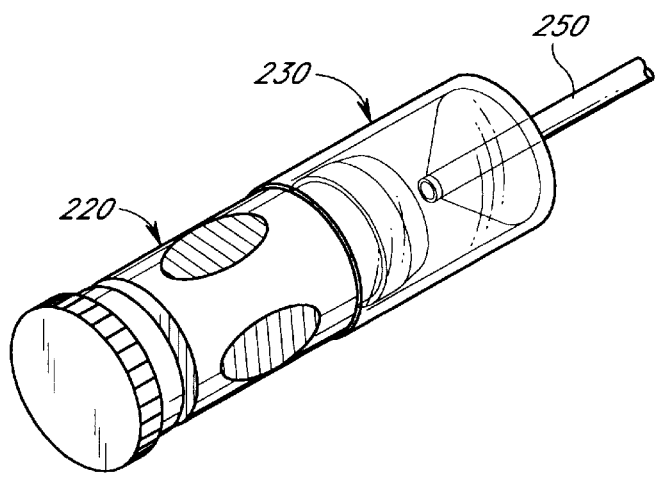
FIG. 10 is a perspective drawing of an assembled booster and adaptor with a lumen inserted in the opening of the adaptor.
Figure 11:
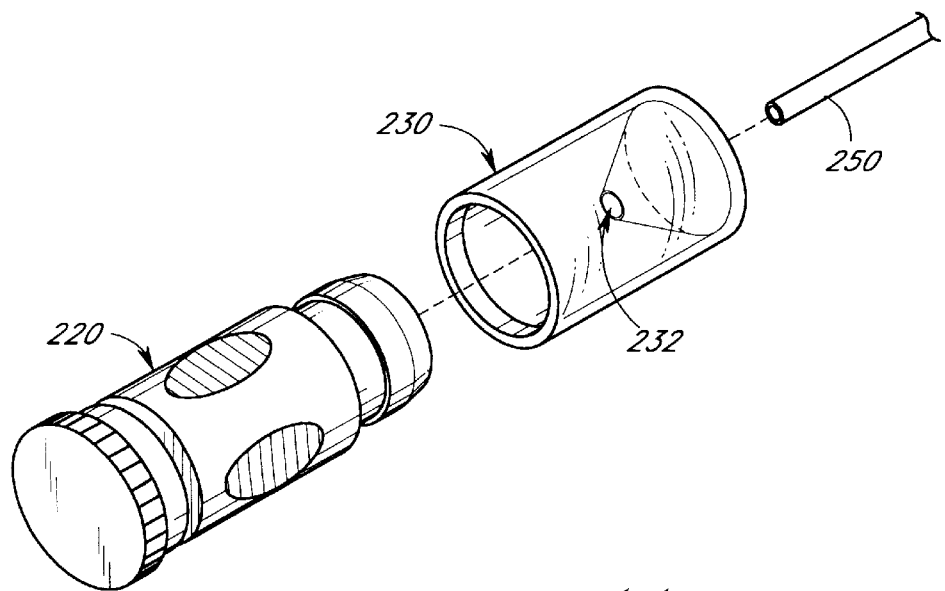
FIG. 11 is an exploded perspective drawing of the booster, adaptor, and lumen.

FIG. 10 shows an adaptor assembly including an adaptor and a booster. FIG. 11 is an exploded view, showing the various parts of the apparatus. A booster 220 is attached to an adaptor 230. A lumen 250 is inserted into an opening 232 of the adaptor 230. The opening 232 is normally of slightly smaller diameter than the outer diameter of the lumen 250 so that there is a snug fit between the inside of the opening 232 and the outside of the lumen 250.

Two forms of the booster 220 are described in detail in U.S. Pat. No. 5,580,530, herein incorporated by reference. Briefly, the booster 220 comprises a vessel for containing hydrogen peroxide, a membrane wall capping the vessel containing the hydrogen peroxide, and an opener with a hollow spike which is used to breach the membrane wall to activate the booster so that the hydrogen peroxide can escape from the vessel.

Figure 12A:
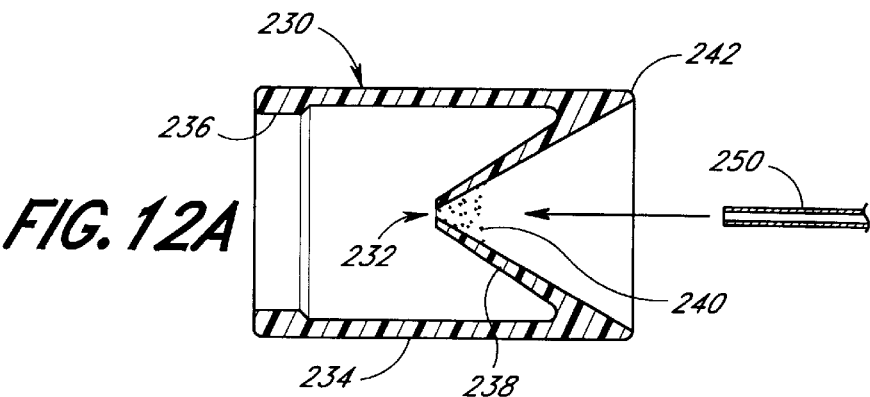
FIG. 12A is a sectional view of the adaptor and lumen, showing how the lumen fits into the opening of the adaptor.

The adaptor 230 is shown in more detail in FIG. 12A herein. The adaptor 230 comprises a cylindrical tubular body 234, an inwardly facing annular flange 236 for firmly attaching the cylindrical tubular body 234 to the booster 220, a truncated cone 238, the opening 232, and texturing 240 on the outer surface of the truncated cone 238 surrounding the opening 232. The adaptor has one or a combination of the following properties.

First, texturing can be added to the contact surface. The texturing can take various forms such as ridges, concentric rings, uneven surfaces, projections having equal heights, projections with varying heights, etc. Whatever form of texturing is used, there can be a plurality of the ridges, rings, or projections of equal or varying heights. The height of the texturing varies and is related to the viscosity of the antimicrobial fluid. The height of the texture varies from 0.01 millimeters to 50 millimeters. The height of the texture for an antimicrobial fluid which is a gas will generally be less than for an antimicrobial fluid which is a liquid, because a gas has a lower viscosity than a liquid. Although the height of the texturing can be determined by one skilled in the art, in general, a height of 0.1 millimeter is preferred for an antimicrobial agent which is a gas. The height of the texturing which is preferred for a liquid is normally in the range of 1 to 5 millimeters, depending on the viscosity of the liquid. The texturing also preferably extends to the inside of the opening 232, so that the area directly facing the lumen 250 is textured as well as the outer surface of the truncated cone 238 surrounding the opening 232. The portion of the truncated cone 238 which is textured is in the range of 0.01 to 50 millimeters, radially extending from the edge of the opening 232. The inwardly facing annular flange 236 fits into a shallow annular groove on the booster 220 when the adaptor 30 is fitted into place on the booster, thereby firmly attaching the adaptor 230 to the booster 220. Those of skill in the art will appreciate that the dimensions of the truncated cone 238 and the opening 232 can be varied to accommodate various types of instruments to be sterilized.

Second, the material, at least in the contact area, can have minimum chemical and physical interaction with the sterilant or sterilizing agent. Chemical interaction includes chemical reaction or catalytic decomposition of the sterilant. Physical interaction includes absorption or adsorption of the sterilant by the material. Third, the material, at least in the contact area, can be permeable to the sterilant so that the antimicrobial fluid can penetrate through the material.

Suitable materials for fabricating the adaptor, at least in the contact area, can include, but are not limited to, polyolefins (including thermoplastic elastomers), fluorinated and/or chlorinated polyolefins (including thermoplastic elastomers), fluorovinylidene, chlorovinylidene, liquid crystal polymers such as wholly aromatic polyester or polyesteramide, silicone rubber, or fluorinated silicone rubber. These materials can be mixed with one or more fillers which have minimum chemical/physical interactions with the chemical sterilant. Fillers are usually added to enhance mechanical, electrical, or thermomechanical properties. These materials are also suitable for the contact surface of the previously described openings of the interface and the holders.

The following procedure may be used when sterilizing equipment with the booster 220 and the adaptor 230. An appropriately sized adaptor 230 is selected for the particular lumen 250 or other equipment to be sterilized. The adaptor 230 is attached to the booster 220, and the lumen 250 or other instrument to be sterilized is inserted into the opening 232. The booster 220 is activated, and the hydrogen peroxide or other sterilizing agent is free to enter the adaptor 230 and the interior of the lumen 250 or instrument. In general practice, the activated booster 220, adaptor 230, and lumen 250 are placed into a sterilization chamber, the chamber is sealed, and the chamber is evacuated, preferably to 100 torr or less. An antimicrobial fluid is then injected into the chamber, where it vaporizes and contacts the exposed surface of the equipment. Various factors known to those skilled in the art can be used to enhance sterilization such as heat, plasma, or high frequency radiation.

The hydrogen peroxide or other antimicrobial fluid in the booster 220 volatilizes when the chamber is evacuated and enters the adaptor 230 and the lumen 250, thereby sterilizing the interior of the lumen. The exterior of the lumen is sterilized by the antimicrobial agent which is injected into the chamber.

Figure 12B:
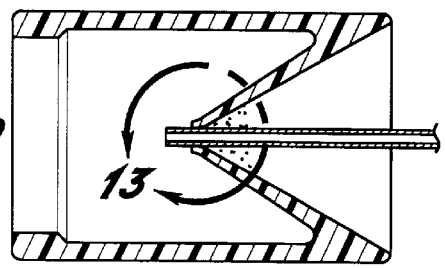
FIG. 12B is a sectional view of the adaptor and lumen, with the lumen inserted into the opening of the adaptor.

FIGS. 12A and 12B illustrate the use of the adaptor 230 with a lumen 250. One skilled in the art can appreciate that the size of the opening 232 on the adaptor can be varied, depending on the size of the lumen or other equipment connected to the adaptor 230. The body of the adaptor can have shapes other than a cylinder, depending on the shape of the booster. For example, a rectangular adaptor would be used if the booster were rectangular. Similar modifications would be obvious to those skilled in the art.

Figure 13:
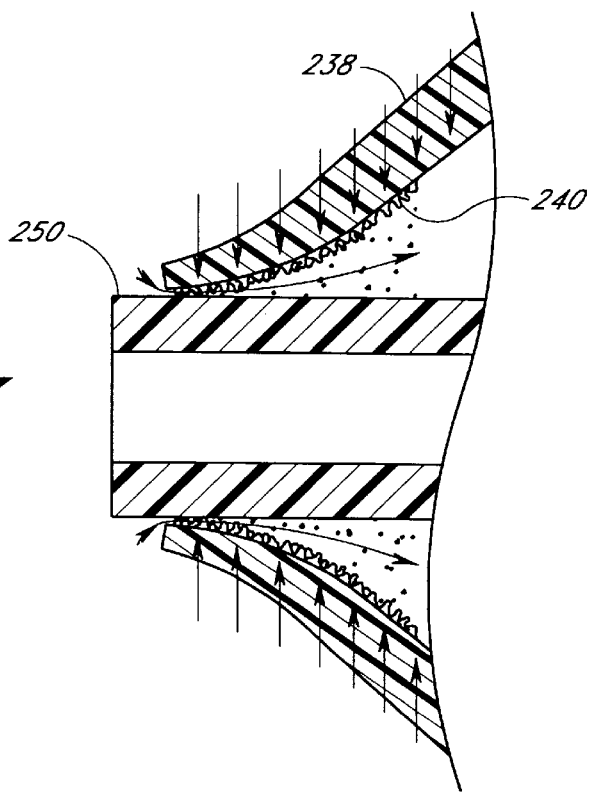
FIG. 13 is a blow-up of FIG. 12B showing a sectional view of the area of contact between the adaptor and the lumen, the flow of the sterilant vapor through the textured area of the adaptor and through the material of the adaptor is shown with arrows.

The adaptor 230 can have several features which make the sterilization of the lumen even more effective than with previous devices. Some of these features are illustrated in FIG. 13, which is a blowup of FIG. 12B, showing the area of contact between the lumen 250 and the adaptor 230. First, the areas of contact between the adaptor 230 and the lumen 250 or other medical device can be reduced by using textured surfaces on the adaptor 230. Thus, the opening 232 and the part of the truncated cone 238 which can contact the lumen 250 can be textured. This is shown on FIG. 13. Only the tips of the texturing devices remain as areas of contact between the adaptor 230 and the lumen 250. This contact area is far less than if the texturing were not present. In addition, there are small gaps between the ridges or "bumps", which create an uneven surface. The antimicrobial agent can enter these gaps and reach areas which would otherwise be inaccessible.

Finally, if the material used to construct the adaptor 230 is permeable to the antimicrobial agent, typically hydrogen peroxide, peracetic acid, or chlorine dioxide, further enhancement of the sterilization effectiveness can be achieved. The antimicrobial agent thus penetrates the adaptor 230 to reach any areas of contact between the adaptor 230 and the lumen 250 or other instrument which remain after these contact areas are minimized through surface texturing. FIG. 13 shows arrows illustrating the penetration of the sterilant vapor to the contact areas both through the gaps between the unevenness of the texturing and through the permeable material from which the adaptor 230 can be fabricated.

The effectiveness of penetration of the antimicrobial agent through the material of the adaptor to the contact areas can be even further enhanced by making the adaptor thinner in the contact areas than in the remainder of the adaptor. For example, in FIGS. 12A and 13, the wall thickness of the truncated cone 238 of the adaptor 230 decreases from the outer end 242 to the opening 232. The portion of the truncated cone 238 which is in contact with the lumen 250 is the thinnest part of the truncated cone, and the antimicrobial agent can penetrate to the contact area between the adaptor and the lumen more effectively than if the adaptor in this area were thicker. Making the adaptor thinner in the contact areas than in the remainder of the adaptor is a way to further enhance the penetration of the antimicrobial agent through the material of the adaptor into the contact area. Although this is a preferred embodiment, it is not a required feature.

By using one or a combination of these features in the adaptor 230, the antimicrobial agent can penetrate the areas of contact between the adaptor 230 and the lumen 250 more effectively than in previous designs. These features include: applying texture or uneven surfaces to the contact area so as to reduce surface contact and enhance bidirectional diffusion of sterilant; using a material which has minimal chemical and physical interaction with the sterilant; and forming the adaptor from a material that is permeable to the sterilant so that the sterilizing agent can penetrate the material.

The methods of the present invention can be used whenever there are areas of contact between an article to be sterilized through sterilization and a connecting device for the article. Often, the connecting device will have an aperture through which the article is inserted. There are areas of contact between the aperture of the connecting device and the article to be sterilized. The article to be sterilized can comprise a lumen, rod, or other device. The methods of the present invention can be used in the connecting device and/or the article to be sterilized. These methods include the use of texturing on the areas of the connecting device which contact the device to be sterilized in order to reduce the contact area between the article and the connecting device. Second, the connecting device can be made of a material which is permeable to the antimicrobial agent so that any remaining contact surfaces can be sterilized by penetration of the antimicrobial agent through the material of the adaptor. Third, the selected material can be a material which has minimal physical and chemical interaction with the antimicrobial agent. Ways to optimize these design modifications will be apparent to those skilled in the art.

These methods can also be used to enhance the penetration of antimicrobial agent to contact areas within a medical device. Often a medical device is made of two or more pieces. There are likely to be contact areas between the pieces from which the medical device is formed. One example of a medical device made up of two or more pieces and having contact areas is a pair of forceps. The methods of the present invention can be used to enhance the penetration of the antimicrobial agent to these contact areas.

One or more of the pieces forming the medical device can incorporate the features of the present invention to enhance the penetration of the antimicrobial agent to the contact areas. These features include the use of texturing or uneven surfaces on one or more of the pieces forming the medical device in the contact areas between the two or more pieces. The texturing will help to reduce the contact area. Second, one or more of the pieces forming the medical device, at least in the contact area, can be made of a material which is permeable to the antimicrobial agent. Third, the material selected to form one or more of the pieces forming the medical device, at least in the contact area, can be a material which has minimal physical and chemical interaction with the antimicrobial agent. Any one or a combination of these features can be used to enhance the penetration of the antimicrobial agent to the contact areas between the two or more pieces forming a medical device.

The antimicrobials used with the methods and devices of the various embodiments of the present invention include solutions of glutaraldehyde, hydrogen peroxide, chlorine dioxide, peracetic acid, or other antimicrobials in an inert medium. Although high concentrations of the antimicrobial agents are more effective, material compatibility and handling problems may arise at high concentrations.

The present invention has been described above. Many modifications and variation of the cleaning/sterilizing or cleaning/disinfecting process and the apparatus in such process may be made without departing substantially from the spirit and scope of the present invention. Accordingly, it should be clearly understood that the form of the invention described and illustrated herein is exemplary only, and is not intended as a limitation on the scope.

What is claimed is:

1. A system for providing fluid to a device, comprising:
a container having an interface separating a first space from a second space, the interface having at least one opening for receiving the device wherein the opening has an uneven contact surface that contacts the device, forming a contact area with a plurality of contact points or segments, said contact points or segments having sharp edges or sharp points, wherein each sharp edge or sharp point is adapted to minimally contact the surface.

2. The system of claim 1, wherein at least one of the contact points or segments is moveable and separately controllable from the other contact points or segments.

3. The system of claim 1, wherein the interface comprises an adaptor or a connector.

4. The system of claim 1, wherein the interface comprises one or more plates.

5. The system of claim 1, wherein at least two independently controllable apertures are sequentially arranged along and form a portion of the opening.

6. The system of claim 5, wherein at least one of the apertures is formed by a shutter.

7. The system of claim 5, wherein at least one of the apertures is formed by two plates, the surfaces of the plates forming the aperture being equipped with an expandable or compressible material.

8. The system of claim 1, wherein the first and second space is coupled to a vacuum or pressure system for generating a pressure difference between the first and second space.

9. The system of claim 1, wherein the interface is selected from the group consisting of a tray, a mat, a separator, a container, a chamber, and a holder.

10. A system for providing fluid to a device, comprising:
an interface separating a first space from a second space, the interface having at least one opening for receiving the device wherein the opening has a contact surface which contacts the device forming a contact area;
at least two independently controllable apertures which are sequentially arranged along and form a portion of the opening, wherein at least one of the apertures is formed by two plates, the surfaces of the plates forming the aperture being equipped with an expandable or compressible material, wherein each of the apertures defines an elongate cross section having a longitudinal axis as viewed from a direction perpendicular to the surface of the plates, the longitudinal axis of one aperture forms an angle with that of the other aperture, and the two apertures are positioned close enough to each other for the expandable material on one aperture to be brought in contact with the other aperture when the expandable material is expanded.

11. A method for providing fluid to a device in a container comprising the steps of:
a) providing an uneven surface having a contact area, said contact area having a plurality of contact points or segments, said contact points or segments having sharp edges or sharp points wherein each sharp edge or sharp point minimally contacts the device after the device is placed in the container;
b) placing the device in or on the surface such that said device contacts said surface at said contact area; and
c) providing fluid to said device such that said fluid penetrates said contact area and contacts said device.

12. The method of claim 11, wherein in step (a) the means provided on the contact area is a textured surface.

13. The method of claim 11, wherein the surface is selected from the group consisting of a tray, a container, a chamber, a mat, a holder, an adaptor, a connector, a separator.

14. The method of claim 13, wherein the surface is a mat having a plurality of projections thereon, wherein the contact area is on at least one of said projections.

15. The method of claim 11, wherein the fluid comprises a chemical germicide, a wash fluid or a rinse fluid.

16. A method for providing fluid to a device in a container comprising the steps of:
a) providing an interface with an opening therein;
b) placing the device in the opening such that the device contacts the interface at a contact area on the interface;
c) providing the fluid to the device;
d) changing the relative position of the device with respect to said opening without opening the container such that the device does not continuously contact said contact area; and
e) repeating step c) after d).

17. The method of claim 16, wherein step (b) comprises compressing a compressible material.

18. The method of claim 16, wherein in step (e) the relative position is changed by alternately moving a different portion of the contact area of the opening into contact with and, then, away from contact with the device.

19. The method of claim 16, wherein the contact area provides a seal between the opening and the device which selected from the group consisting of a gas-tight seal, a tight-fitting seal, or a loose-fitting seal.

20. The method of claim 16, wherein the surface is selected from the group consisting of a tray, a container, a chamber, a mat, a holder, an adaptor, a connector, a separator.

21. The method of claim 16, wherein the fluid comprises a chemical germicide, a wash fluid or a rinse fluid.

22. The method of claim 16, wherein step (e) comprises opening or closing a shutter.

23. The method of claim 16, wherein the opening comprises a plurality of contact points or segments with said device, and wherein step (e) comprises separately moving and controlling at least one of said contact points or segments.

24. The method of claim 16, wherein step (e) comprises inflating or deflating a layer of expandable material provided on said opening.

25. A method for providing fluid to a device in a container comprising the steps of:
   a) providing an interface with an opening therein;
   b) placing the device in the opening such that the device contacts the interface at a contact area on the interface;
   c) providing the fluid to the device; and
   d) changing the relative position of the device with respect to said opening by adjusting two independently controllable apertures sequentially along the passage of the opening such that the device does not continuously contact said contact area.

26. A method for providing fluid to a device in a container comprising the steps of:
   a) providing an interface with an opening therein wherein the interface comprises at least one plate;
   b) placing the device in the opening such that the device contacts the interface at a contact area on the interface;
   c) providing the fluid to the device; and
   d) changing the relative position of the device with respect to said opening by moving at least one of the plates, such that the device does not continuously contact said contact area.

27. A system for providing fluid to a device, comprising:
   an interface separating a first space from a second space, the interface having at least one opening for receiving the device wherein the opening has an uneven contact surface that contacts the device, forming a contact area with a plurality of contact points or segments, said contact points or segments being made of nonporous material.

28. A method for providing fluid to a device in a container comprising the steps of:
   providing an interface with an opening therein;
   placing the device in the opening such that the device contacts the interface at a contact area on the interface;
   providing the fluid to the device; and
   changing the relative position of the device with respect to the opening without opening the container such that the device does not continuously contact said contact area.

29. An apparatus for providing fluid to a device having a lumen comprising:
   a container having at least one interface dividing said container into two or more compartments;
   at least one opening in said interface;
   a holder sealably coupled to said opening, said holder being openable and closeable while said container is closed.

30. An apparatus of claim 29, wherein said container comprises at least two interfaces with openings therein, each opening comprising a controllable aperture.

31. An apparatus of claim 30, wherein at least one of the apertures comprises a shutter.

32. The system of claim 30, wherein at least one of the apertures comprises two plates with surfaces adjacent to said opening, said surfaces being equipped with an expandable or compressible material.

* * * * *